United States Patent
Valadon

(10) Patent No.: US 11,578,332 B2
(45) Date of Patent: Feb. 14, 2023

(54) METHODS OF RAPID LIGATION-INDEPENDENT CLONING OF DNA AND USES THEREOF

(71) Applicant: GENE INFINITY LLC, San Diego, CA (US)

(72) Inventor: Philippe Valadon, San Diego, CA (US)

(*) Notice: Subject to any disclaimer, the term of this patent is extended or adjusted under 35 U.S.C. 154(b) by 254 days.

(21) Appl. No.: 16/079,515

(22) PCT Filed: Jun. 5, 2017

(86) PCT No.: PCT/US2017/036017
§ 371 (c)(1),
(2) Date: Aug. 23, 2018

(87) PCT Pub. No.: WO2018/013250
PCT Pub. Date: Jan. 18, 2018

(65) Prior Publication Data
US 2020/0017864 A1    Jan. 16, 2020

Related U.S. Application Data

(60) Provisional application No. 62/362,275, filed on Jul. 14, 2016.

(51) Int. Cl.
| | |
|---|---|
| C12N 15/66 | (2006.01) |
| C12N 9/12 | (2006.01) |
| C12N 9/22 | (2006.01) |
| C12N 15/64 | (2006.01) |
| C12N 15/70 | (2006.01) |

(52) U.S. Cl.
CPC .......... C12N 15/66 (2013.01); C12N 9/1252 (2013.01); C12N 9/22 (2013.01); C12N 15/64 (2013.01); C12N 15/70 (2013.01); C12N 2820/55 (2013.01); C12N 2830/55 (2013.01); C12N 2830/85 (2013.01); C12Y 207/07007 (2013.01); C12Y 301/11 (2013.01)

(58) Field of Classification Search
CPC ....... C12N 15/66; C12N 9/1252; C12N 15/64
See application file for complete search history.

(56) References Cited

U.S. PATENT DOCUMENTS

| | | | | |
|---|---|---|---|---|
| 2007/0292954 A1* | 12/2007 | Elledge | .................. | C12N 15/64 435/488 |
| 2010/0035768 A1* | 2/2010 | Gibson | .................. | C12N 15/64 506/17 |
| 2011/0300583 A1* | 12/2011 | Barnes | .................... | C12P 19/34 435/91.2 |

FOREIGN PATENT DOCUMENTS

WO    WO-2016026574 A1 *    2/2016    ............... C12N 9/22

OTHER PUBLICATIONS

Reddy, Processive Proofreading Is Intrinsic to T4 DNA Polymerase, Journal Biological Chemsitry, 267(20): 14157-14166, 1992. (Year: 1992).*
Recombinase RecA [*Thermus thermophilus* HB8], Gene ID: 3168508, NCBI, NLM, NIH, 2020 (Year: 2020).*
Garcia-Nafria, IVA cloning: A single-tube universal cloning system exploiting bacterial In Vivo Assembly, Sci. Rep., 6, 27459, doi: 10.1038/srep27459, 2016. (Year: 2016).*
Garcia-Nafria, IVA cloning: A single-tube universal cloning system exploiting bacterial In Vivo Assembly, Sci. Rep., 6, 27459, doi: 10.1038/srep27459, 2016; Supplementary Material. (Year: 2016).*
Kibbe, OligoCalc: an online oligonucleotide properties calculator, Nucleic Acids Research, 35, W43-W46, 2007. (Year: 2007).*
Islam, Optimizing T4 DNA polymerase conditions enhances the efficiency of one-step sequence- and ligation-independent cloning, BioTechniques, 63: 125-130, 2017 (Year: 2017).*

* cited by examiner

Primary Examiner — Samuel C Woolwine
Assistant Examiner — Carolyn L Greene

(57) ABSTRACT

The present invention generally relates to improved methods of assembly of two or more DNA fragments, methods of rapid ligation-independent cloning, and kits for rapid ligation-independent cloning and their uses.

6 Claims, 9 Drawing Sheets

Specification includes a Sequence Listing.

FIGURE 1A: Principle of Rapid LIC
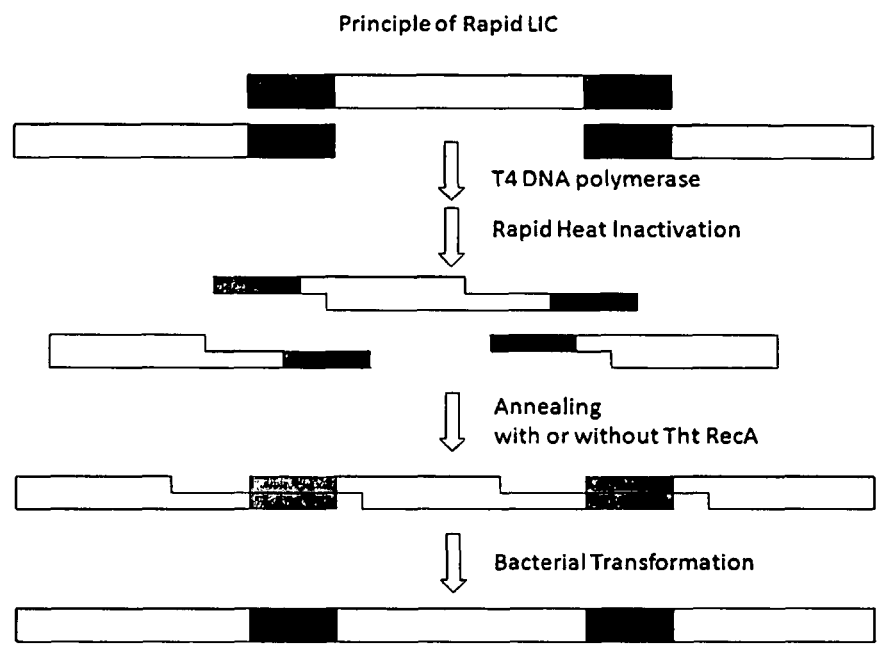

FIGURE 1B: Timeline of Rapid LIC
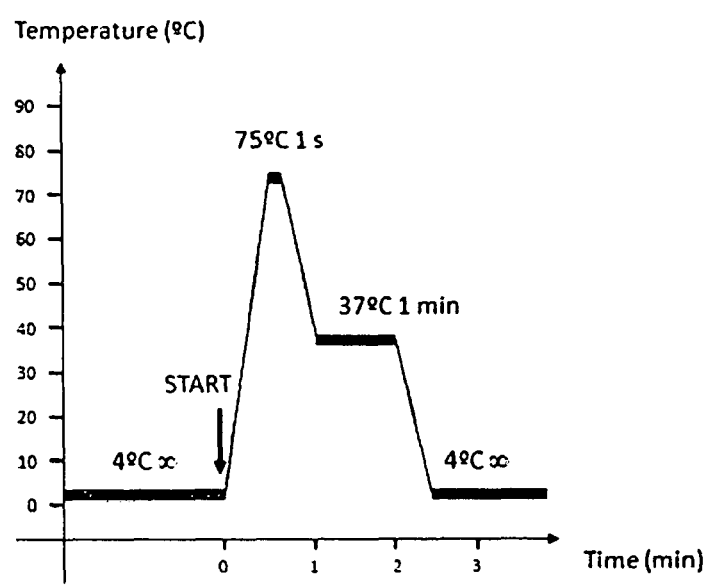

FIGURE 2: Applications of Rapid LIC
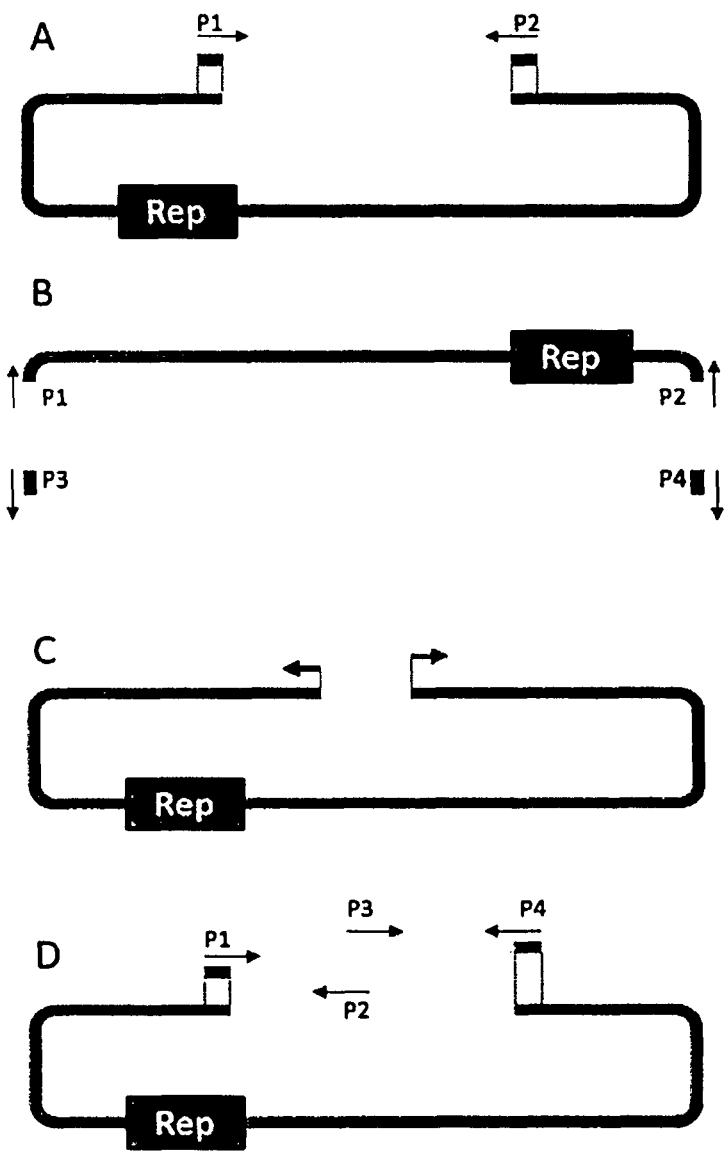

FIGURE 3: Heat Inactivation of T4 DNA Polymerase Exonuclease Activity
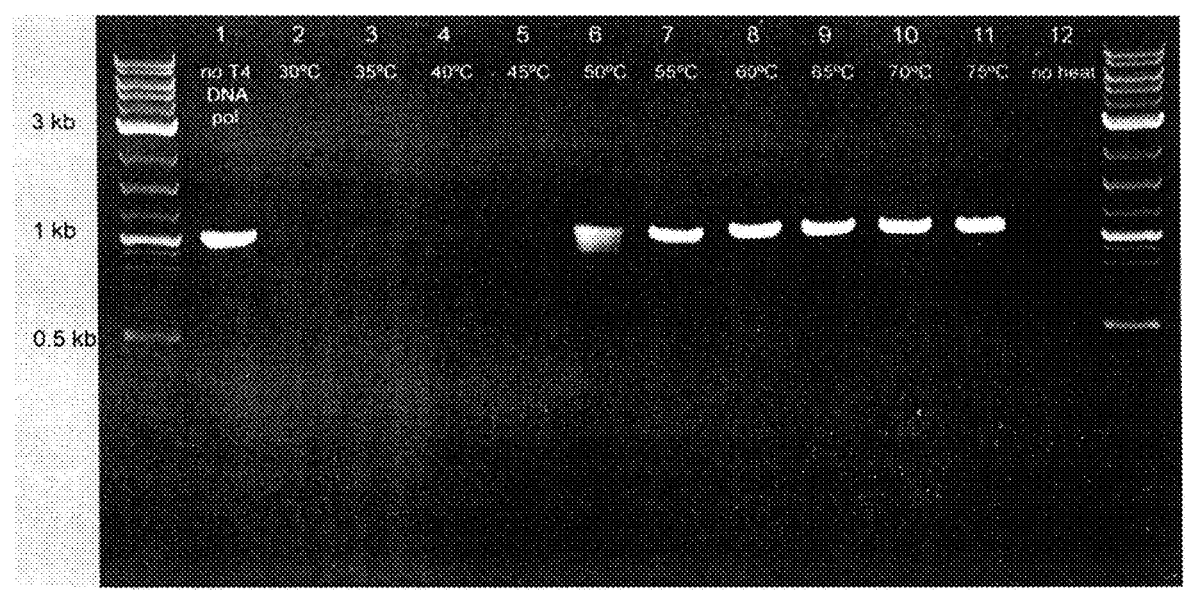

FIGURE 4: T4 DNA Polymerase Exonuclease Inactivation by Heat Pulse
Panel A
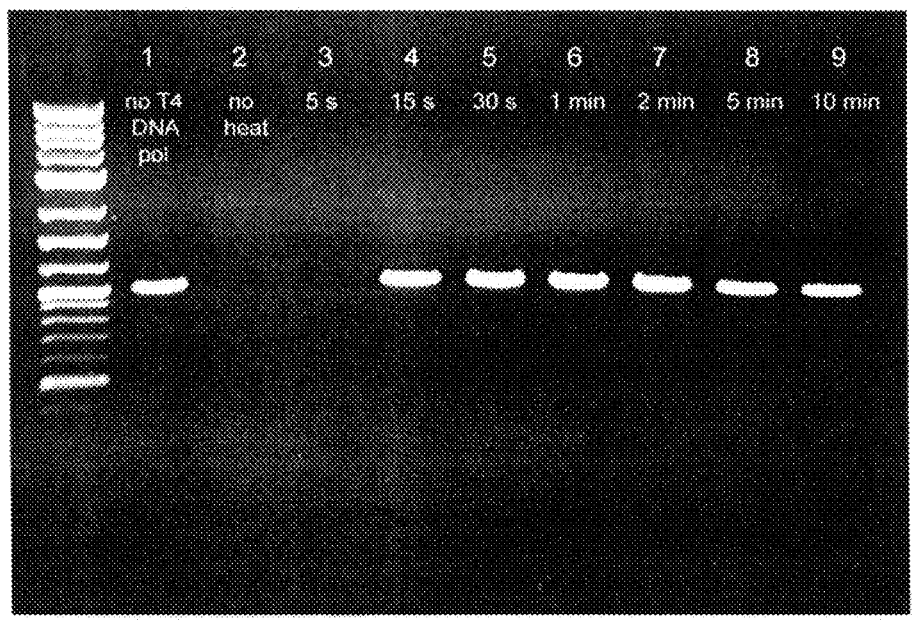
Panel B
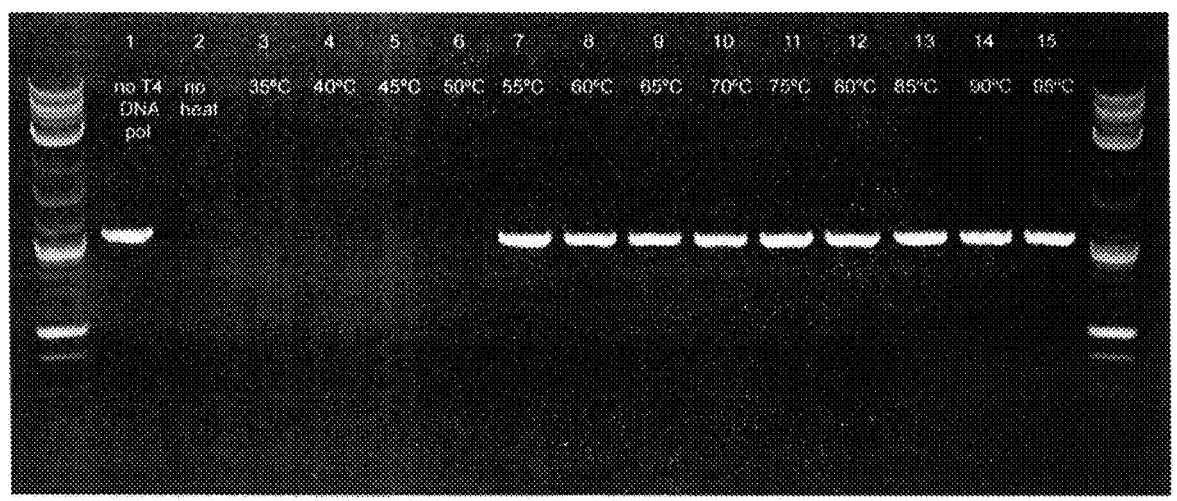

FIGURE 5: Influence of Incubation at 37°C Before Inactivation of T4 DNA Polymerase Exonuclease on LIC Efficiency
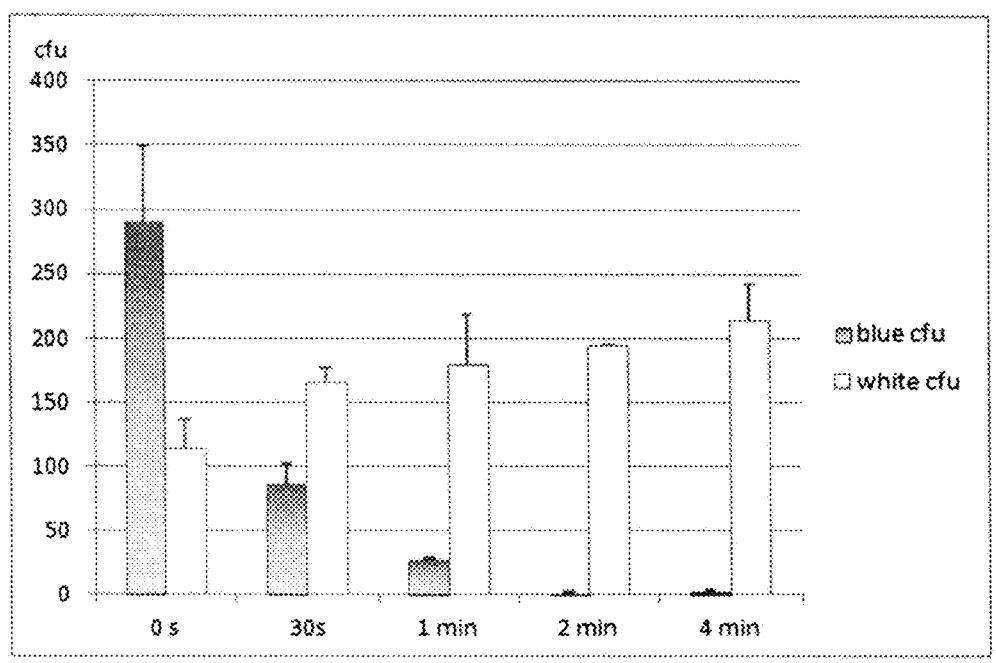

FIGURE 6: Time-Dependence of Annealing
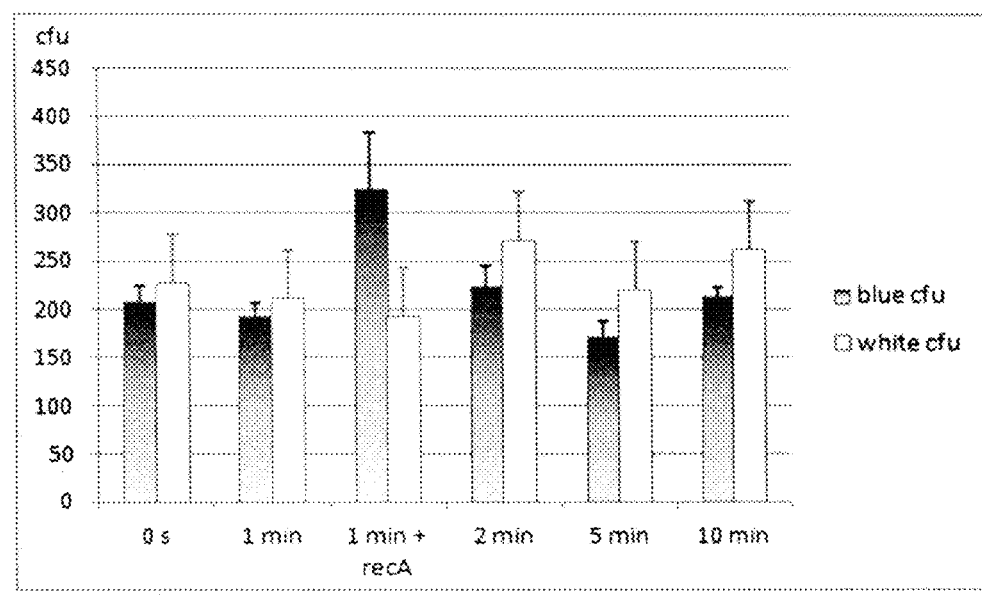

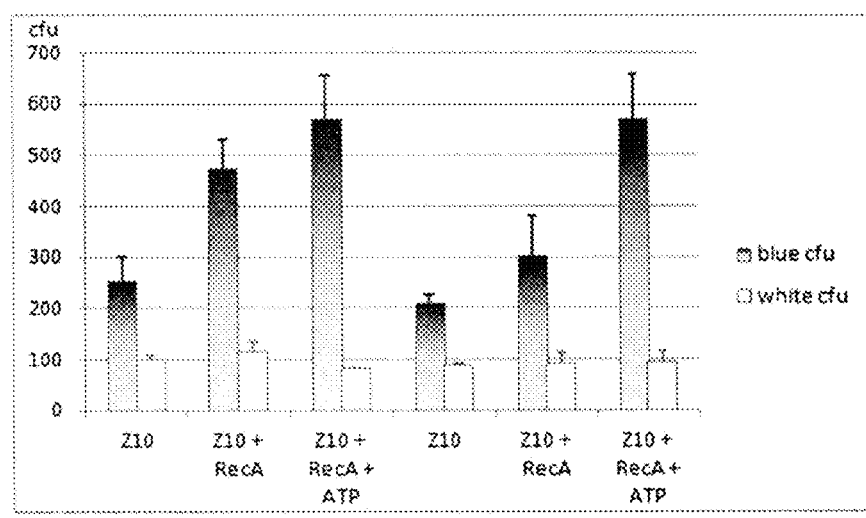
FIGURE 7: Influence of RecA and ATP on Cloning Efficiency

FIGURE 8: Complementary Hemi-PCR Assay
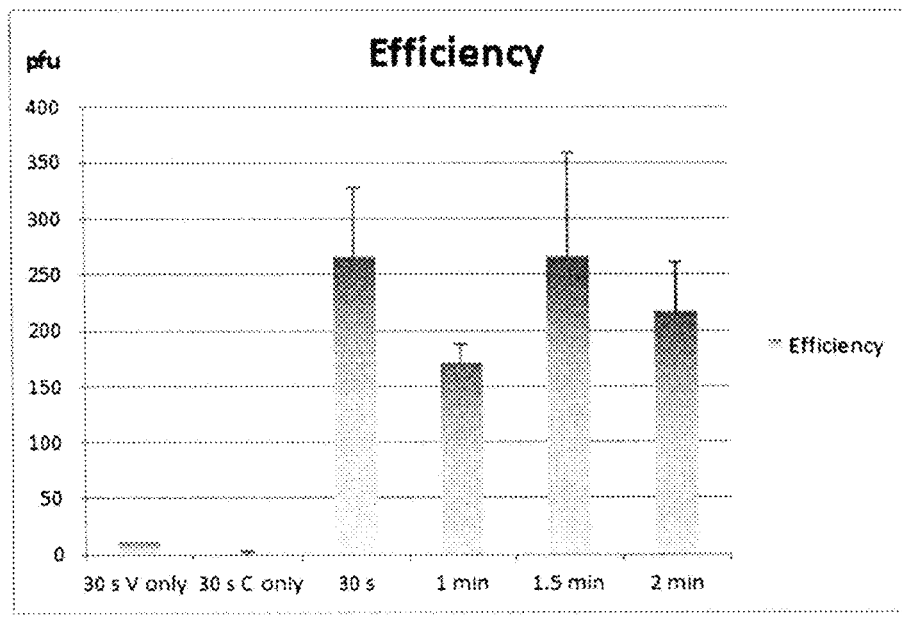

SEQUENCE LISTING

```
<160> NUMBER OF SEQ ID NOS: 30

<210> SEQ ID NO 1
<211> LENGTH: 47
<212> TYPE: DNA
<213> ORGANISM: Artificial Sequence
<220> FEATURE:
<223> OTHER INFORMATION: synthetic DNA fragment

<400> SEQUENCE: 1
tactcgcggc ccagcagtaa caatttcaca caggaaacag ctatgac          47

<210> SEQ ID NO 2
<211> LENGTH: 33
<212> TYPE: DNA
<213> ORGANISM: Artificial Sequence
<220> FEATURE:
<223> OTHER INFORMATION: Synthetic DNA fragment

<400> SEQUENCE: 2
ccaccgcctt ggcctcgcgc gtttcggtga tga                         33

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gaatatttat gacgattccg cagtattg                              28

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
caatactgcg gaatcgtcat aaatattc                              28
```

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
cgcgttaaat ttttgttaaa tcagctc                                              27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gagctgattt aacaaaaatt taacgcg                                              27

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tccaacaaag ccctcccagc                                                      20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gactgtgact ggttagacgc ct                                                   22

<210> SEQ ID NO 9
<211> LENGTH: 885
<212> TYPE: DNA
<213> ORGANISM: Artificial Sequence
<220> FEATURE:
<223> OTHER INFORMATION: synthetic DNA fragment

<400> SEQUENCE: 9
aggcgtctaa ccagtcacag tcgcaagttt aaacggatct ctagcgaatt cggcttgggg          60
atatccacca tggagacaga cactcctg ctatgggtac tgctgctctt agcggcccag           120
ccggccatgg cgcccaatac gcaaaccgcc tctccccgcg cgttggccga ttcattaatg         180
cagctggcac gacaggtttc ccgactggaa agcgggcagt gagcgcaacg caattaatgt         240
gagttagctc actcattagg caccccaggc tttacacttt atgcttccgg ctcgtatgtt         300
gtgtggaatt gtgagcggat aacaatttca cacaggaaac agctatgacc atgattacgg         360
attcactggc cgtcgtttta caacgtcgtg actgggaaaa ccctggcgtt acccaactta         420
atcgccttgc agcacatccc ctttcgcca gctggcgtaa tagcgaagag gcccgcaccg          480
atcgcccttc ccaacagttg cgcagcctga attaaaatag ataggggcccg ggaggccccg        540 agcccaaatc ttctgacaaa actcacacat gcccaccgtg cccagcacct gaactcctgg        600
ggggaccgtc agtcttcctc ttccccccaa acccaagga caccctcatg atctcccgga         660

```
cccctgaggt cacatgcgtg gtggtggacg tgagccacga agaccctgag gtcaagttca    720
actggtacgt ggacggcgtg gaggtgcata atgccaagac aaagccgcgg gaggagcagt    780
acaacagcac gtaccgtgtg gtcagcgtcc tcaccgtcct gcaccaggac tggctgaatg    840
gcaaggagta caagtgcaag gtgtccaaca agccctccc agccc                     885

<210> SEQ ID NO 10
<211> LENGTH: 52
<212> TYPE: DNA
<213> ORGANISM: Artificial Sequence
<220> FEATURE:
<223> OTHER INFORMATION: primer

<400> SEQUENCE: 10
tgctgctctt agcggcccag ccggccatgg cggatattgt gctaactcag tc             52

<210> SEQ ID NO 11
<211> LENGTH: 48
<212> TYPE: DNA
<213> ORGANISM: Artificial Sequence
<220> FEATURE:
<223> OTHER INFORMATION: primer

<400> SEQUENCE: 11
aagatttggg ctcggggcct cccgggcctg cagagacagt gaccagag                  48

<210> SEQ ID NO 12
<211> LENGTH: 720
<212> TYPE: DNA
<213> ORGANISM: Artificial Sequence
<220> FEATURE:
<223> OTHER INFORMATION: synthetic DNA fragment

<400> SEQUENCE: 12
gatattgtgc taactcagtc tccagccacc ctgtctgtga ctccaggaaa tagcgtcagt    60
ctttcctgca gggccagcca agtattggc aacaacctac actggtatca acaaaaatca    120
catgagtctc caaggcttct catcaagtat gcttcccagt ccatctctgg gatcccctcc    180
aggttcagtg gcagtggatc aggacagat ttcactctca gtatcaacag tgtggagact    240
gaagattttg gaatgtattt ctgtcaacag agtaacagct ggccttacac gttcggaggg    300
gggaccaagc tggaaataaa aggtggtggt ggttctggtg gtggtggttc tggcggcggc    360
ggctccggtg gtggtggatc cgacgtgcag cttcaggagt caggacctag cctcgtgaaa    420
ccttctcaga ctctgtccct cacctgttct gtcactggcg actccatcac cagtgattac    480
tggagctgga tccggaaatt cccagggaat agacttgagt acatggggta cgtaagctac    540
agtggtagca cttactacaa tccatctctc aaaagtcgaa tctccatcac cgagacaca    600 tccaagaacc agtactacct ggatttgaat tctgtgacta ctgaggacac agccacatat    660
tactgtgcaa actgggacgg tgattactgg ggccaaggga ctctggtcac tgtctctgca    720

<210> SEQ ID NO 13
<211> LENGTH: 79
<212> TYPE: DNA
<213> ORGANISM: Artificial Sequence
<220> FEATURE:
<223> OTHER INFORMATION: synthetic DNA fragment

<400> SEQUENCE: 13
cagtcactat gaatcaacta cttagatggt attagtgacc tgtatctaga atttttgtc    60
```
atcaaacctg tcgcactcc                                                79

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
tggtattagt gacctgtaac agagcattag cgcaaggtga tttttgtctt              50

<210> SEQ ID NO 15
<211> LENGTH: 44
<212> TYPE: DNA
<213> ORGANISM: Artificial Sequence
<220> FEATURE:
<223> OTHER INFORMATION: primer

<400> SEQUENCE: 15
gtttgatgac aaaaaattag cgcaagaaga caaaaatcac cttg                    44

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gcatccacca agggcccatc                                               20

<210> SEQ ID NO 17
<211> LENGTH: 68
<212> TYPE: DNA
<213> ORGANISM: Artificial Sequence
<220> FEATURE:
<223> OTHER INFORMATION: primer

<400> SEQUENCE: 17
aggtcggggg atctgcggcc gctcatgtgt gagttttgtc acaagatttg ggctcaactt   60
tcttgtcc                                                            68

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ttctgtgttc tctccacagg                                               20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gcatccacca agggcccatc                                               20

<210> SEQ ID NO 20
<211> LENGTH: 16

```
<212> TYPE: DNA
<213> ORGANISM: Artificial Sequence
<220> FEATURE:
<223> OTHER INFORMATION: primer

<400> SEQUENCE: 20
gcagatcccc cgacct                                                      16

<210> SEQ ID NO 21
<211> LENGTH: 15
<212> TYPE: DNA
<213> ORGANISM: Artificial Sequence
<220> FEATURE:
<223> OTHER INFORMATION: synthetic DNA fragment

<400> SEQUENCE: 21
tactcgcggc ccagc                                                       15

<210> SEQ ID NO 22
<211> LENGTH: 15
<212> TYPE: DNA
<213> ORGANISM: Artificial Sequence
<220> FEATURE:
<223> OTHER INFORMATION: synthetic DNA fragment

<400> SEQUENCE: 22
ccaccgcctt ggcct                                                       15

<210> SEQ ID NO 23
<211> LENGTH: 28
<212> TYPE: DNA
<213> ORGANISM: Artificial Sequence
<220> FEATURE:
<223> OTHER INFORMATION: sythetic DNA fragment

<400> SEQUENCE: 23
gaatatttat gacgattccg cagtattg                                         28

<210> SEQ ID NO 24
<211> LENGTH: 27
<212> TYPE: DNA
<213> ORGANISM: Artificial Sequence
<220> FEATURE:
<223> OTHER INFORMATION: synthetic DNA fragment

<400> SEQUENCE: 24
gagctgattt aacaaaaatt taacgcg                                          27

<210> SEQ ID NO 25
<211> LENGTH: 22
<212> TYPE: DNA
<213> ORGANISM: Artificial Sequence
<220> FEATURE:
<223> OTHER INFORMATION: synthetic DNA fragment

<400> SEQUENCE: 25
aggcgtctaa ccagtcacag tc                                               22

<210> SEQ ID NO 26
<211> LENGTH: 22
<212> TYPE: DNA
<213> ORGANISM: Artificial Sequence
<220> FEATURE:
<223> OTHER INFORMATION: synthetic DNA fragment

<400> SEQUENCE: 26
```

```
tccaacaaag ccctcccagc cc                                              22

<210> SEQ ID NO 27
<211> LENGTH: 18
<212> TYPE: DNA
<213> ORGANISM: Artificial Sequence
<220> FEATURE:
<223> OTHER INFORMATION: synthetic DNA fragment

<400> SEQUENCE: 27
tgctgctctt agcggccc                                                   18

<210> SEQ ID NO 28
<211> LENGTH: 20
<212> TYPE: DNA
<213> ORGANISM: Artificial Sequence
<220> FEATURE:
<223> OTHER INFORMATION: synthetic DNA fragment

<400> SEQUENCE: 28
aagatttggg ctcggggcct                                                 20

<210> SEQ ID NO 29
<211> LENGTH: 18
<212> TYPE: DNA
<213> ORGANISM: Artificial Sequence
<220> FEATURE:
<223> OTHER INFORMATION: synthetic DNA fragment

<400> SEQUENCE: 29
tggtattagt gacctgta                                                   18

<210> SEQ ID NO 30
<211> LENGTH: 17
<212> TYPE: DNA
<213> ORGANISM: Artificial Sequence
<220> FEATURE:
<223> OTHER INFORMATION: synthetic DNA fragment

<400> SEQUENCE: 30
ctttgatgac aaaaaat                                                    17
```

METHODS OF RAPID LIGATION-INDEPENDENT CLONING OF DNA AND USES THEREOF

CROSS REFERENCE TO RELATED APPLICATION(S)

This is a US national phase application under 35 U.S.C. § 371 of international patent application no. PCT/US2017/036017, filed Jun. 5, 2017, which itself claims priority to U.S. provisional patent application No. 62/362,275, filed Jul. 14, 2016. All of the applications referred to in this paragraph are incorporated by reference in their entireties herein.

REFERENCE TO SEQUENCE LISTING

The official copy of the sequence listing is submitted electronically via EFS-Web as an ASCII formatted sequence listing with the file "ADL-PCT_ST25" created on Jun. 1, 2017, filed on Jun. 5, 2017 and having a size of 8 KB. The sequence listing contained in this ASCII formatted document forms part of the specification and is herein incorporated by reference in its entirety.

FIELD OF THE INVENTION

The present invention generally relates to improved very rapid methods of assembly of two or more DNA molecules in the field of recombinant DNA technology, methods of rapid ligation-independent cloning, and kits for rapid ligation-independent cloning and their uses.

BACKGROUND OF THE INVENTION

A. DNA Cloning

DNA cloning is the procedure of making copies (or clones) of particular DNA sequences, usually by insertion into a cloning vector and replication into a host organism. Molecular cloning regroups the set of operations needed to assemble and clone recombinant DNA fragments for the purpose of DNA cloning; it usually involves methods to generate DNA fragments and varied strategies to assemble them with a vector that can be further amplified into the host. Traditionally, DNA cloning was made with the use of restriction enzymes (Cohen et al. 1973). Typically, the DNA to clone is cut on each end by a restriction enzyme, the vector is cut by the same enzyme, usually in an area named the multi-cloning site (MCS) and the two fragments are joined together by treatment with a DNA ligase. The use of two restriction enzymes with non-compatible overhangs allows directional cloning in which the DNA fragments is inserted into the vector in only one direction.

Cloning methods were later developed with the availability of the polymerase chain reaction (PCR). PCR enables de novo synthesis of DNA fragments in vitro by exponential amplification of a DNA sequence. A PCR uses a DNA template, two small oligonucleotides called primers whose sequence matches the DNA template on each end of the sequence to amplify, and a series of multistep temperature cycles comprising a denaturation step to separate the two DNA strands, an annealing step where primers find their homologous sequence on DNA, and finally, a step of synthesis or elongation by the means of a DNA polymerase in the presence of dNTPs. If restriction sites are introduced in the primer sequence, PCR fragments can be cloned by traditional restriction enzyme cloning. Alternatively, a blunt-ended PCR product can be cloned directly in an open vector after ligation with the DNA ligase, but not directionally. The use of Taq DNA polymerase often leaves an extra A nucleotide on the 3' end which limits the blunt-end cloning efficiency. This problem led to the popular T/A cloning method in which a free T overhang generated by a restriction enzyme digestion on the vector conveniently creates a one-base complementary overhang for cloning. All these methods require at some point the use of a DNA ligase to join DNA fragments, even when multiple PCR fragments are combined by Splicing by Overlap Extension PCR (Horton R M et at 1989).

B. Ligation-Independent Cloning

The need for restriction sites and the inherent issues associated with the length of traditional cloning has led to the development of numerous alternate strategies that did not require a DNA ligation step. For purposes of clarity and relevance to this invention, ligation-independent cloning or "LIC", is defined as any cloning method that uses the complementary annealing of sequence-specific single-stranded stretches of DNA located on each end of the DNA fragments for the joining reaction; the stretches must be long enough to hold the DNA assembly together through the transformation process. Note that a few modern cloning methods often use the term, seamless cloning, to be differentiated from the older ligation-independent cloning term, still the event at the source of the DNA joining reaction is the annealing between two complementary stretches of single-stranded DNA "ssDNA" that are physically created during the process. Some authors also use the term, homologous recombination, to highlight the sequence homology between the DNA fragments but the joining reaction is again physically accomplished by the annealing of complementary stretches of ssDNA. The procedure is de facto well-adapted for the cloning of PCR inserts where homologies can be incorporated in the primer sequence Ligation-Independent Polymerase Chain Reaction, "LIC-PCR". In most applications, the stretches of ssDNA are generated by the 3' to 5' exonuclease activity found in proof-reading polymerases, such as for example T4 DNA polymerase, but other enzymes have been used with success such as lambda exonuclease, an enzyme with a 5'→3' exo activity (Tsen 1999). The filling of the gaps left by the annealing of partially overlapping ssDNA tails and ligation per see can occur either in vitro before transformation or in vivo after transformation in the bacterial host with the help of the DNA repair system. It has been shown indeed that the host bacterium fills up the resulting sequence gaps and ligates the construct very efficiently. There are very few by-products, in particular no by-products, resulting from improper ligations. The sequence-dependency of the process makes the cloning very reliable and efficient. The procedure mimics to some extent natural recombination processes used by live cells to repair, mix, and/or exchange DNA molecules.

The first documented report of LIC was made by Aslanidis (Aslanidis et al. 1990). Specially designed vectors with two 12-nucleotide (nt) stretches of DNA containing four nucleotides but one, located on each side of the cloning site were used. Digestion with a 3'→5' exonuclease in the presence of the complementary nucleotide triphosphate would continue until the first occurrence of the missing base was encountered (event which kicks off the polymerase activity), thus allowing fine control of the stretches of homologous ssDNA (Aslanidis et al. 1990; Haun et al. 1992; Kuijper et al. 1992). In the sequence and ligation-independent cloning or, SLIC method, (Li et al. 2007), all dNTPS were initially excluded to allow sequence-independent overlaps to be created, and dCTP was then added to bring the T4 DNA polymerase to a stall at the first G occurrence and the LIC proceeded as usual.

The minimal length requirement for LIC was found to be 10-nt long (Aslanidis et al. 1994). Improved cloning efficiency was observed between 15-nt and 30-nt (Sharon et al., U.S. Pat. No. 6,372,429), but stretches as long as 100 nt have been reported (Elledge, US Patent Application US 2007/0292954 A1). In a similar situation intermediate between classical cloning and LIC, Stoker et al. were able to apply the Aslanidis method to generate a 2-nt overhang but a final step of DNA ligation was still required for cloning (Stocker et al. 1990).

An alternative method to generate ssDNA tails for cloning PCR products is to mix PCR fragments of unequal length. The method was used in rolling circle PCR, "RCPCR", where both vector and insert are amplified and annealed before transfection (Jones et al. 1990a and 1990b). In this enzyme-free cloning method, Tillet et al. mixed PCR products of different lengths to achieve similar results (Tillet et al. 1999); in a comparable approach, the "mixed-PCR" reaction used multiple nested PCR products (Tachibana et al. 2009). The inverse-PCR, "iPCR", method achieved the same goal by using incomplete PCR products generated towards the end of amplification and found in any PCR reaction (Li et al. 2007).

Many other ways to create ssDNA tails have been described. The use of nicking endonuclease, meaning enzymes that cut only one strand, has been reported (Yang 2010). The use of deoxyuracil residues "dU" incorporated in primers and secondary enzymatic removal by the uracil DNA glycosylase has been reported several times, although for the generation of smaller sticky tails (see e.g. Bitinaite et al. 2007). The presence of abasic sites (sites with no base) induces a stall of the DNA polymerase and, when properly located in primers, creates stretches of ssDNA at the ends of the PCR products; this approach was used in the AS-PCR (autosticky PCR, Gal et al. 1999). The use of primers containing ribonucleotides has been applied to LIC as well (Donahue et al. 2002).

The vaccinia virus DNA polymerase can catalyze in vivo the formation of DNA concateners (Willer et al. 2000). This DNA joining reaction is dependent of the exonuclease activity of the polymerase and is preceded by the formation of complementary ssDNA tails (Hamilton et al. 2007). The reaction can proceed at room temperature without the need for any particular step to inactivate the exonuclease and has been applied to the cloning of DNA fragments (Evans et al. U.S. Pat. No. 7,575,860).

It was shown early after the discovery of LIC that ssDNA stretches can be generated by controlled 3'→5' exonuclease digestion. Typically, one used the 3'→5' exonuclease activity of T4 DNA polymerase or of Exonuclease III. The method required a delicate control of the reaction because of the high processivity of those enzymes and variations from batch to batch between enzyme preparations. The last point was reported by Kuijper et al. (1992) who, while proceeding with LIC following the original Aslanidis method, noticed that each lot of T4 DNA polymerase had to be tested, likely for contamination by endonuclease activity. In Hsiao et al. (1993), linearized vectors and PCR inserts were purified and mixed in equal molar amounts, then treated by ExoIII for 30 s to 1 min on ice; after adding TE (Tris/EDTA buffer), the remaining ExoIII was immediately removed by phenol/chloroform extraction. Kaluz et al. (1992) reported a similar approach but only the insert was treated by ExoIII and, following phenol/chloroform extraction, ligated to a cut vector o/n at 16° C.; in this case a ligation step was necessary because of the very short overhangs on the vector side. Li et al. (1997) also used ExoIII followed by phenol/chloroform extraction before annealing and transformation and demonstrated that both 5' overhangs and gaps can be left for repair by the host bacteria.

A very similar approach using T4 DNA polymerase was published in 1993 (Yang et al. 1993). Following controlled treatment for 2 min at 37° C., the T4 DNA polymerase was inactivated at 70° C. for 10 min. The authors then filled-in the gaps after annealing using again T4 polymerase in the presence of dNTP. It was suggested that the fill-in step may be omitted but the assumption was not verified experimentally. The method was patented under U.S. Pat. No. 5,580,759. The Gibson assembly goes one step further by ligating the DNA assembly before transformation, thus enabling the cloning of very large DNA molecules (Gibson 2011).

The present invention addresses a need in the art for more efficient and faster methods in cloning techniques.

SUMMARY OF THE INVENTION

The inventor has discovered that the exonuclease activity of known exonucleases, such as T4 DNA polymerase, can be inactivated by heat at a much more rapid rate than currently reported in the literature. This property can be applied to greatly shorten the time to clone DNA by LIC, which allows the processing of many more samples in less time whether manual or automated processes are used.

T4 DNA polymerase is the 3'→5' exonuclease most often used to create single-stranded homologous recesses to assemble DNA fragments. It is reported widely in the literature that heat inactivation of T4 DNA polymerase takes between 10 min and 20 min at 70° C. or 75° C. T4 DNA polymerase has two distinct enzymatic activities, a 5'→3' DNA polymerase activity which requires a DNA template, dNTP and a primer to catalyze the synthesis of a template-dependent DNA strand, and a 3'→5' exonuclease activity, which is template-independent. After careful examination of the literature, the rate of inactivation and temperature dependence of the 3'→5' exonuclease activity of T4 DNA polymerase has not been studied or reported, and most likely all requirements for heat-inactivation of this enzyme are indeed based solely on the results of inactivation studies of the 5'→3' DNA polymerase activity. Confirming this observation is that activity measurements for purified T4 DNA polymerase by suppliers are reported for a 5'→3' polymerization activity. Logically, people who used T4 DNA polymerase for DNA cloning by LIC followed the supplier-recommended inactivation temperature in their experiments. For example, U.S. Pat. No. 5,580,759 requires a heat inactivation of 10 min at 70° C. for T4 DNA polymerase enzyme.

It was discovered that two novel conditions to inactivate T4 DNA polymerase exonuclease activity by heat treatment. First, incubation of T4 DNA polymerase between 50° C. and 65° C. leads to inactivation of the exonuclease activity; this is up to 15° C. lower than existing art. Second, it was discovered that a brief heat pulse at around 50° C. and higher leads to inactivation of the exonuclease activity within a very brief period of time as short as 10 s. This represents up to a two log difference shorter compared with what is currently accepted in the field for T4 DNA polymerase.

The present invention provides improved methods for LIC and kits for LIC comprising a step of heat inactivation or, heat inactivation step, at temperature lower than 65° C. In one aspect, the heat inactivation of T4 DNA polymerase is between about 50° C. and 65° C.; in another aspect, the heat inactivation of T4 DNA polymerase is between about 50° C. and 60° C.; in yet another aspect, the heat inactivation of T4 DNA polymerase is between about 50° C. and 55° C.

The present invention provides improved methods for LIC and kits for LIC comprising a step of rapid heat inactivation of the exonuclease. In some embodiments the heat inactivation of T4 DNA polymerase is for a period of less than ten minutes between about 50° C. and 95° C. In a preferred embodiment of the above method, the heat inactivation is for a period of less than five minutes at a temperature between about 50° C. and 95° C. In some embodiments the heat inactivation is for a period of less than one minute at a temperature between about 50° C. and 95° C. In some preferred embodiments, the heat inactivation is for a period of inactivation no longer than about 10 s between about 50° C. and 95° C.

The time gained to inactivate the exonuclease activity translates into much shorter time to complete an LIC reaction which allows many more samples to be processed in less time than prior methods currently in use. In some embodiments, the present invention provides methods for rapid LIC that can be completed in less than ten minutes. In some embodiments, the present invention provides methods for rapid LIC that can be completed in less than five minutes. In some embodiments, the present invention provides methods for rapid LIC that can be completed in no longer than three minutes. In some embodiments, the present invention provides methods for rapid LIC that can be completed in about one minute.

In a more general manner, our discovery on the heat-dependence of exonuclease activity is likely true for many if not all proofreading polymerases. Noteworthy is the inactivation times reported for enzymes exhibiting only exo activity that have been used for LIC (e.g. exonuclease III, lambda exonuclease) are similar to the time reported for T4 DNA polymerase and it is not excluded that analysis of their rate of heat-inactivation reveals much shorter inactivation times. Preferably, the exonuclease used in the method of the invention is T4 DNA polymerase, however other enzymes with exonuclease activity include, but are not limited to, *E. coli* polI, vaccinia virus DNA polymerase, lambda exonuclease, exonuclease III, and T7 exonuclease. Some embodiments of the present invention further comprise the use of costimulatory factors. In some embodiments of the present invention, the costimulatory factors are ssDNA binding proteins. Examples of single stranded binding proteins include, but are not limited to, *E. coli* SSB, RecA and its homolog RAD51 in human, Tth RecA, human replication protein hRPA, herpes simplex virus 1CP8 protein, yRPA, vaccinia virus single strand binding protein, and extreme thermostable single-stranded DNA binding protein, "ET SSB", a thermostable single-stranded DNA binding protein. In some embodiments, the ssDNA binding protein is thermostable enough to resist inactivation during the heat pulse given to inactivate the exonuclease. In some embodiments of the present invention, the costimulatory factor is Tth RecA, the RecA homolog isolated from *Thermus thermophilus*, a thermostable RecA. In some embodiments, the invention further comprises ATP. In some embodiments, the present invention provides a kit for cloning comprising T4 polymerase, thermostable RecA, and ATP.

A rapid LIC kit will contain the 2 or more fragments of DNA to assemble, T4 DNA polymerase, Tth RecA and ATP. Both DNA fragments share homologous sequences, 15 to 20 nucleotides long, on both ends so that the melting temperature of the homologous sequences will not be higher than 65° C. to allow complete denaturation at 75° C. The reagents are combined on ice in a PCR tube and placed on a PCR machine pre-cooled at 4° C. A short program, overall less than 5-min long, consists in a temperature ramp to 75° C., long enough to create recessed ends on all DNA fragments, inactivate the exonuclease activity and denature the homologous tails, followed by a temperature decrease to 37° C. during which Tth RecA associates with ssDNA. Finally, the mixture is incubated for 1 min at 37° C. to allow assembly of homologous ssDNA stretches and cooled at 4° C. to stop the reaction. The overall reaction is less than 5-min long to as short as between 2 and 3 min on some automated thermocyclers. The reaction mixture can be used immediately to transform competent bacteria to isolate recombinant clones containing the 2 or more DNA fragments properly assembled.

BRIEF DESCRIPTION OF THE DRAWINGS

FIG. 1A is a schematic representation of the rapid LIC method of the present invention.

FIG. 1B is an illustration of the temperature ramp and timeline for the rapid LIC reaction.

FIG. 2 summarizes four panels with distinct applications of the rapid LIC method. Panel A illustrates the cloning of a PCR fragment amplified by primers P1 and P2 or a synthetic DNA fragment into an open vector. Panel B illustrates the Complementary Hemi-PCR (CH-PCR) reaction where the 2 halves of a vector are amplified by PCR and recombined with modifications and/or mutations at the overlapping junctions. Panel C illustrates the cloning of 2 short complementary oligonucleotides. Panel D illustrates the cloning of multiple PCR fragments into an open vector. Shared regions of sequence homology are highlighted by small areas with different shades at the ends of DNA fragments; the replication of origin is indicated by a box with the symbol Rep.

FIG. 3 is an electrophoresis gel showing the results from Example 1 of the present specification. FIG. 3 shows the inactivation at different target temperatures of the T4 DNA polymerase exonuclease activity. Each lane shows DNA digested by T4 DNA polymerase exonuclease activity after treatment at different temperatures. The far left and right lanes show DNA ladders. Lane 1 is a control with no T4 DNA polymerase showing the undigested DNA. Lane 2 shows T4 DNA polymerase exonuclease activity when the target temperature was 30° C. Lanes 3-12 show the exonuclease activity after the T4 DNA polymerase reached target temperatures 35° C., 40° C., 45° C., 50° C., 55° C., 60° C., 65° C., 70° C., 75° C., and no heat respectively.

FIG. 4 is an electrophoresis gel showing the results of Example 2 of the present specification. FIG. 4 shows the rate of T4 DNA polymerase exonuclease inactivation by a heat pulse. Panel A shows the rate of inactivation at 75° C. The far left lane shows a DNA ladder and Lane 1 shows DNA with no T4 DNA polymerase added; Lane 2 shows DNA with T4 polymerase and no heat, Lane 3 to Lane 9 shows DNA with T4 DNA polymerase raised to 75° C. for 5 seconds, 15 seconds, 30 seconds, 1 minute, 2 minutes, 5 minutes, and 10 minutes, respectively. Panel B shows the rate of inactivation for a 10 s heat pulse at varied temperatures. The far left lane shows a DNA ladder and Lane 1 shows DNA with no T4 DNA polymerase added; Lane 2 shows DNA with T4 polymerase and no heat, Lane 3 to Lane 15 shows DNA with T4 DNA polymerase raised for 10 s at 35° C., 40° C., 45° C., 50° C., 55° C., 60° C., 65° C., 70° C., 75° C., 80° C., 85° C., 90° C. and 95° C., respectively.

FIG. 5 is a graph of the blue cfu and white cfu colony data from the blue-white screening assay in Example 3. These data show the effect of a variable pre-heat inactivation 37° C. plateau on cloning efficiency of 0 seconds, 30 seconds, 1 minute, 2 minutes, and 4 minutes, respectively.

FIG. 6 is a graph of the blue cfu and white cfu colony data from the blue-white screening assay in Example 4. These data show the effect of a variable post-heat inactivation 37° C. temperature plateau on cloning efficiency.

FIG. 7 is a graph of the blue cfu and white cfu colony data from the blue-white screening assay in Example 5.

FIG. 8 is a graph of the cloning efficiency from the Complementary Hemi-PCR (CH-PCR) assay in Example 6.

DETAILED DESCRIPTION OF THE INVENTION

Detailed descriptions of preferred embodiments are provided herein. It is to be understood however, that the present invention may be embodied in various forms. Therefore, specific reference to various forms are provided as a basis for the claims and for teaching one skilled in the present art to employ the present invention in appropriate system, structure, or manner. Although any methods, devices, and materials similar or equivalent to those described herein can be used in the practice or testing of the invention, the preferred methods, devices and materials are now described.

A. Definitions

For clarity of disclosure, and not by way of limitation, the detailed description of the present invention is divided into the subsections that follow.

Unless defined otherwise, all technical and scientific terms used herein have the same meaning as is commonly understood by one of ordinary skill in the art to which this invention belongs. All patents, applications, and other publications referred to herein are incorporated by reference in their entirety. If a definition set forth in this section is contrary to or otherwise inconsistent with a definition set forth in the patents, application, published applications, and other publications that are herein incorporated by reference, the definitions set forth in this section prevail over the definition that is incorporated by reference.

As used herein, "a" or "an" means "at least one" or "one or more". The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The practice of the present invention may employ conventional techniques and descriptions of bacteriology, molecular biology (including recombinant techniques), cell biology, and biochemistry, which are within the skill of the art. Such conventional techniques include PCR, extension reaction, oligonucleotide synthesis and oligonucleotide annealing. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y. all of which are herein incorporated in their entirety by reference for all purposes.

As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions.

As used herein, the term "amplifying" refers to a process whereby a portion of a nucleic acid is replicated using, for example, any of a broad range of primer extension reactions. Exemplary primer extension reactions include, but are not limited to, PCR. Unless specifically stated, "amplifying" refers to a single replication or to an arithmetic, logarithmic, or exponential amplification.

As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur.

The terms "amplification cycle" and "PCR cycle" are used interchangeably herein and as used herein refers to the denaturing of a double-stranded polynucleotide sequence followed by annealing of a primer sequence to its complementary sequence and extension of the primer sequence.

The terms "polymerase" and "nucleic acid polymerase" are used interchangeably and as used herein refer to any polypeptide that catalyzes the synthesis or sequencing of a polynucleotide using an existing polynucleotide as a template.

The term "polynucleotide" refers in particular to double-stranded DNA, double-stranded RNA, hybrid DNA/RNA duplex, single-stranded DNA and single-stranded RNA.

As used herein, "DNA polymerase" refers to a nucleic acid polymerase that catalyzes the synthesis or sequencing of DNA using an existing polynucleotide as a template.

As used herein, the term "exonuclease" refers to any polypeptide that catalyzes the sequential cleavage of nucleotides one at a time from one end of a polynucleotide chain.

B. Rapid Ligation-Independent Cloning ("LIC")

The present invention relates to a novel method to clone DNA by LIC using rapid heat inactivation of the exonuclease enabling the joining of two or more DNA fragments in a very short experimental time. This invention is a direct improvement of the LIC method developed by Yang and collaborators (Yang et al. 1993 and U.S. Pat. No. 5,580,759).

In the most common application of DNA cloning by the Yang method, two DNA molecules share sequence homologies so that the ends of one fragment are complementary to the ends of the other fragment. These DNA fragments can be generated either by digestion with restriction enzymes of larger fragments, PCR of a DNA template, or direct synthesis with no other sequence requirements than the terminal sequence homologies. The method consists in a controlled digestion of each fragment by a strand-specific exonuclease (e.g. 3'-5' exonuclease activity of T4 DNA polymerase) creating single stranded DNA overhangs on each end. Following inactivation of the exonuclease activity by prolonged heat treatment, the overhangs are then annealed together respectively of their sequence complementarity to create circular joined DNA molecules that can be used to transform bacterial host and clone the DNA. The initial assumption that gaps left by imperfect annealing could be repaired by the bacterial host, thus omitting in vitro fill-in reaction and ligation, has been verified experimentally since.

The method of the present invention is called rapid LIC. The principle of rapid LIC and its timeline are illustrated on FIGS. 1A and 1B. In the most common application, the rapid LIC method will join two DNA molecules for the purpose of DNA cloning. The first step incorporates two DNA molecules sharing sequence homologies so that each end of one fragment is homologous to one end of the other fragment. The second step utilizes an exonuclease to create strand-specific recessed ends on both ends of each DNA fragment; the exonuclease is then rapidly inactivated by a short heat pulse. The third step consists of an annealing reaction to create circular close DNA molecules and is followed by a transformation of a bacterial host to initiate DNA repair and replication.

FIG. 2 illustrates the main applications of rapid LIC. In one embodiment (Panel A) one DNA fragment is a vector opened by digestion with restriction enzymes and the other DNA fragment is a PCR product. The primers P1 and P2 are made of two separate areas; the 5' terminal regions are homologous to the DNA sequence to amplify and the 3' proximal region share sequence homologies with the vector sequence on either side of the restriction cuts. Instead of a PCR product, the fragment to insert in the vector could be also a synthetic DNA fragment or the product of the assembly by SOE-PCR of multiple PCR fragments. In another embodiment (Panel B), the DNA fragments are amplified from a single vector and a new vector is created by the rapid LIC method; by carefully choosing the proximal and distal regions of the primers, it is possible to create a deletion, introduce a mutation or insert new sequences in the original vector. This method is called, the CH-PCR for Complementary Hemi-PCR. In another embodiment (Panel C), one DNA fragment is a vector open after digestion with restriction enzymes and the other results from the annealing of two partially overlapping oligonucleotides. Most if not all DNA cloning methods using exonuclease recession cannot clone small oligonucleotides because of their rapid disappearance from the reaction mixture; because the rapid LIC method is very fast, it is still efficient to run it twice back to back; during the first run the cut vector is added and recessed ends are generated; after adding the two oligonucleotides, the reaction is run again but the oligonucleotides are not destroyed because the exonuclease activity has been inactivated. In another embodiment (Panel D), multiple DNA fragments are cloned at once in an open vector. Each DNA fragment, including the vector itself, is terminated by a small sequence that is homologous to the beginning of the next fragment; indeed all homology regions taken two by two among all DNA fragments create a unique close circular DNA molecule after conjoint annealing.

C. Rapid Exonuclease Inactivation

It is widely reported in the literature that heat inactivation of T4 DNA polymerase requires exposure of between 10 and 20 min at temperatures between 70° C. and 75° C. For example, 10 min at 70° C. is reported in U.S. Pat. No. 5,580,759; New England Biolabs (Ipswich, Mass.), a reference company in the field of molecular biology, indicates 75° C. for 20 min for inactivation, while Thermo Fisher Scientific Inc. and Promega Corporation (Fitchburg, Wis.) recommend 10 min at 75° C.; the lowest temperature reported is 65° C. for 10 min by EURx Ltd. (Poland), a molecular biology supplier. It was discovered that T4 DNA polymerase exonuclease activity was instead inactivated at temperatures as low as 50° C.; that is 15° C. to 20° C. below most recommend temperatures for inactivation (Example 1). It is not excluded that in these conditions, the 5'→3' polymerase activity still remains potent. Therefore, the exonuclease activity of T4 DNA polymerase appears extremely sensitive to elevated temperature. This novel characteristic led to the analysis of the inactivation of T4 DNA polymerase exonuclease activity by brief heat pulse. Time-course experiments revealed that complete inactivation was occurring between 5 s and 15 s exposure of the exonuclease at 75° C. (Example 2, Panel A); for a constant heat pulse of 10 s, inactivation appears at 50° C. and above (Example 2, Panel B). This represents up to a two-log difference with what is currently accepted in the field. Because a major trend in modern molecular biology is the shortening of experimental time, this discovery opens the possibility to shorten dramatically the time required for cloning DNA.

The DNA polymerases that may be used in the method of the invention include all DNA polymerases having intrinsic exonuclease activity, preferably 3'→5' exonuclease activity, that can be inactivated rapidly by heat in the conditions indicated in the above embodiments. Such polymerases may be easily identified by assaying the heat-induced inactivation of the exonuclease activity as described in Example 1 and Example 2A and 2B. This group includes but is not limited to T4 DNA polymerase, *E. coli* polI, Klenow fragment, vaccinia virus DNA polymerase, lambda exonuclease, exonuclease III, and T7 exonuclease.

D. Length of Homology

The length of the complementary nucleotide sequences located on the ends of each DNA molecule may be between 5 and about 100 nucleotides, preferably between about 10 and about 35 nucleotides, and most preferably between 15 and 20 nucleotides.

In some embodiments, the length of the complementary nucleotide sequences is between 15 and 20 nucleotides with a melting temperature (Tm) equal or lower than 65° C. The Tm is defined as the temperature at which the folded fraction is 0.5 (Mergny and Lacroix 2003). The conditions to determine Tm are those classically used for preparing a PCR with a sodium concentration of 50 mM and a primer concentration between 0.2 μM and 0.25 μM; Tm of short oligonucleotides between 10 and 100 nucleotides can be estimated with good accuracy using nearest neighbor calculations (Breslauer et al. 1986; SantaLucia J Jr. 1998). Tools to do these calculations are widely available; for example OligoAnalyzer is made available by Integrated Technologies, Inc. and OligoCalc is a free and widely available oligonucleotide properties calculator software (Kibbe 2007). In this range of Tm, the corresponding folded heterodimers are melted at 75° C. Taking the examples of this invention and estimating Tm using OligoAnalyzer and enthalpies using OligoCalc, it was determined that the unfolded fraction at 75° C. using the equations reported by Böttcher et al. (2005) (Table I). All sequences in this range of lengths and temperatures have an unfolded fraction near 100%; oligonucleotides longer than 20 with Tm lower than 65° C. are still almost completely unfolded while those with a Tm above 65° C., in this a case the model oligonucleotides polyG(15) and polyG(20), have a significant folded fraction. It should also be noted that because of the experimental difficulties of analyzing melting curves, it is virtually impossible to measure folded fractions experimentally above 97% (Mergny and Lacroix 2003). Because of the much lower concentration of DNA fragments in the rapid LIC reaction mixture than in a PCR reaction, the actual Tm is in fact lower than the values used in these calculations, which are in consequence underestimating the exact unfolded fraction. Therefore, successful cloning events using the rapid LIC invention in this embodiment will result from annealing events that occurred after the heat pulse and full denaturation of all DNA fragments.

E. Costimulatory Factors

Some embodiments of the present invention further comprise costimulatory factors. In some embodiments of the present invention, the costimulatory factors are single strand DNA binding proteins (SSB). Examples of SSB include, but are not limited to, RecA in *E. coli* and its homolog RAD51 in human. RecA is an ssDNA-dependent ATPase that catalyses the pairing and exchange of DNA strands bearing sequence homologies; its association with DNA is tighter in the presence of ATP (reviewed in Kowalczykowski 1992). It was also discovered that the rate of rapid LIC by homologous recombination is increased by RecA alone and further enhanced after adding ATP. In some embodiments of the present invention, the costimulatory factor is Tth RecA, the RecA homolog isolated from *Thermus thermophilus*, a thermostable RecA whose activity can survive a heat pulse at 75° C. In some embodiments the invention further comprises ATP. In some embodiments the present invention provides a kit for cloning comprising T4 DNA polymerase, thermostable RecA, and ATP.

F. Overall Method

A rapid L1C cloning reaction will contain two fragments or more of DNA to assemble, T4 DNA polymerase, Tth RecA and ATP. Both DNA fragments are sharing homologous sequences, between 5 and about 100 nucleotides on both ends, preferably between about 10 and about 35 nucleotides, and most preferably between 15 and 20 nucleotides, with a Tm each equal or lower than 65° C. The Tm are estimated as described previously using nearest-neighbor calculations in PCR conditions. The reagents are combined on ice in a PCR tube and placed on a thermal cycler (or thermocycler or PCR machine) pre-cooled at 4° C. A short program, overall less than 3-min long, consists in a 1 s plateau at 75° C. followed by a 1 min plateau at 37° C. before the temperature is cooled back at 4° C. (FIG. 1B). The ramp from 4° C. to 75° C. takes about 30 seconds (s) and is long enough to create recessed ends of all DNA fragments. The time to go back and forth between 70° C. and 75° C. is about 10 s, long enough to inactivate of the exonuclease and separate all ssDNA homologous tails. The ramp between 75° C. and 37° C. takes about 30 s during which Tth RecA associates with ssDNA. Finally, the mixture is incubated for 1 min at 37° C. to allow assembly of homologous ssDNA tails and cooled at back at 4° C. to stop the reaction. The overall reaction from the start of the temperature ramp to the return at 4° C. is no longer than 3 min (see timing chart below). The reaction mixture can be used immediately to transform competent bacteria to isolate recombinant clones containing the DNA fragments properly assembled. It is possible to replace the thermal cycler by short heat pulses using pre-heated water baths and complete the reaction in shorter times. Inactivation of T4 DNA polymerase will occur after 10-15 s treatment at 50° C. and above; melting of ssDNA tails will occur above 65° C., at best around 75° C. in a few seconds. Association with Tth RecA will be optimal between 65° C. and 75° C. while annealing between complementary ssDNA tails will mostly occur below 65° C.

Timing Chart.

Time was counted from the start of the temperature raise and measured at passage at 75° C. (time 1), start of 1 minute plateau at 37° C. (time 2), end of 37° C. plateau (time 3) and program arrest (back to 4° C., time 4) on varied instruments:

| Instrument | Time 1 | Time 2 | Time 3 | Time 4 | Total |
| --- | --- | --- | --- | --- | --- |
| PCR Machine 1 | 36 s | 70 s | 127 s | 165 s | 2:45 min |
| PCR Machine 2 | 32 s | 60 s | 118 s | 157 s | 2:37 min |
| Average | 34 s | 65 s | 122.5 s | 161 s | 2:41 min |

G. Kits

Also provided are kits. Such kits can include the compositions of the present invention and, in certain embodiments, instructions for administration. Such kits can facilitate performance of the methods described herein. When supplied as a kit, the different components of the composition can be packaged in separate containers and mixed immediately before use. Components include, but are not limited to DNA fragments, a vector, an exonuclease, an SSB, ATP, and a concentrated reaction buffer, each as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampoules may contain a lyophilized component and in a separate ampoule, sterile water, sterile saline or sterile each of which has been packaged under a neutral non-reacting gas, such as nitrogen. Ampoules may consist of any suitable material, such as glass, organic polymers, such as polycarbonate, polystyrene, ceramic, metal or any other material typically employed to hold reagents. Other examples of suitable containers include bottles that may be fabricated from similar substances as ampoules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

EXAMPLES

The following examples are offered to illustrate, but not to limit the claimed invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

Example 1

Heat-Mediated T4 DNA Polymerase Exonuclease Inactivation

This example demonstrates the rapid inactivation of T4 DNA polymerase exonuclease activity by exposure to heat above 50° C. and below 70° C. It is widely accepted and taught in the literature that T4 DNA polymerase requires at minimum 10 minutes of incubation at 70° C. to become inactive. These previously reported values are believed to be relevant for both polymerase and exonuclease activities. This experiment tested variable target temperature values programmed into a PCR machine initially set at 4° C. After loading the samples containing only T4 DNA polymerase, the thermal cycler rose to a target temperature value and after a one (1) second plateau, samples were rapidly cooled back to 4° C. A test DNA fragment was then added to each sample and after 15 min incubation at 37° C., the DNA was analyzed by electrophoresis on a 1.5% agarose gel. Any remaining exonuclease activity would digest the DNA from both ends, thus creating a smear on the gel, while no exonuclease activity would leave the test DNA intact as a discrete band on the gel.

The test DNA fragment added was Z900. Z900 was generated by amplifying a 966 bp fragment from pUC119 vector with the primers laczbw_r and laczbw_s. The PCR product was re-suspended in water at ~50 ng/μl after purification over a NucleoSpin column from Macherey Nagel (Germany).

```
                                               (SEQ ID NO: 1)
laczbw_s
5'-TACTCGCGGCCCAGCAGTAACAATTTCACACAGGAAACAGCTATGAC (SEQ ID NO: 2)
laczbw_r
5'-CCACCGCCTTGGCCTCGCGCGTTTCGGTGATGA
```

The T4 DNA polymerase mix was prepared by mixing the following on ice:

| Component | Volume |
|---|---|
| Buffer 10x | 10 μl |
| T4 DNA Polymerase (New Englands Biolabs, Ipswich, MA) | 10 μl |
| H2O | 80 μl |

The mixture was distributed into PCR tubes by 15 μl aliquot; the tubes were then successively placed in a PCR machine pre-cooled at 4° C. and the temperature was rapidly increased to one of the variable target temperatures (30° C., 35° C., 40° C., 45° C., 50° C., 55° C., 60° C., 65° C., 70° C., 75° C., no heat). Once the temperature had reached the expected value, the samples were brought back to 4° C. after a one (1) second-long plateau and then placed on ice.

Then 0.5 μl of 10× reaction buffer and 4.5 μl of purified Z900 DNA (~200 ng) were mixed with 5 μl of reaction buffer for each of the variable target temperature points and incubated for 15 minutes at 37° C. The digested DNA was then analyzed by electrophoresis on a 1.5% agarose gel.

The results from this experiment are shown in the gel electrophoresis in FIG. 3. The lanes are numbered from left (lane 1) to right (lane 12) and flanked by DNA ladders. The DNA fragment was clearly visible in the absence of T4 DNA polymerase (lane 1) and exhibited significant digestion in absence of heat treatment (lane 12). Exonuclease activity was easily visible at 30° C. to 45° C. and showed a clear transition around 50° C. (lane 6). At 55° C. and above no exonuclease activity was detectable.

This experiment shows that the exonuclease activity of T4 DNA polymerase was rapidly and irreversibly inactivated above 50° C.

Example 2

Measure of the Rate of Inactivation of T4 DNA Polymerase Exonuclease Activity This experiment was designed to analyze the rate of heat inactivation of T4 DNA polymerase exonuclease activity.

First a mixture containing T4 DNA polymerase 5 μl, 10× buffer 5 μl and water 40 μl was kept on ice. For each time measurement, 5 μl were aliquoted into a tube and incubated for a given period of time in a thermostated block and put back on ice. Then 5 μl of a mixture containing purified Z900 DNA, 10× buffer 6 μl and water 30 μl was added to each tube and assayed for exonuclease activity after 15 minutes at 37° C. before analysis by gel electrophoresis (100 ng DNA per tube, 1 tube per lane). Results are shown in FIG. 4, Panel A. The time points measured were no heat, 5 seconds, 15 seconds, 30 seconds, 1 minute, 2 minutes, 5 minutes, and 10 minutes with no T4 DNA polymerase and no heat as controls. The electrophoresis gel in FIG. 4, Panel A shows in its lanes respectively 1) no T4 DNA polymerase, 2) T4 DNA polymerase with no temperature increase, 3) T4 DNA polymerase 5 seconds at 75° C., 4) T4 DNA polymerase 15 seconds at 75° C., 5) T4 DNA polymerase 30 seconds at 75°

C., 6) T4 DNA polymerase 1 minute at 75° C., 7) T4 DNA polymerase 2 minutes at 75° C., 8) T4 DNA polymerase 5 minutes at 75° C., 9) T4 DNA polymerase 10 minutes at 75° C. Inactivation of the exonuclease activity occurred rapidly between 5 s and 15 s exposure to 75° C.

Second, the same experiment was repeated using a constant heat exposure of 10 seconds and a variable target temperature between 35° C. and 95° C. by 5° C. increment. FIG. 4, Panel B shows the result of the analysis by gel electrophoresis. Inactivation of the exonuclease activity was observed at 50° C. and was complete at 55° C. and above.

Example 3

Influence of Incubation Time Before Inactivation of the Exonuclease

In this experiment, the influence of the length of incubation at 37° C. before heat inactivation of the T4 DNA exonuclease activity on the efficiency of cloning was analyzed. A blue-white colony assay was used following the approach developed by Thieme (Thieme et al. 2001) and used a PCR machine to control temperature.

Blue-White Cloning Assay

The PCR product Z900 was treated by DpnI restriction enzyme to remove the DNA template and re-suspended in water at 10 ng/µl after purification over a Macherey Nagel NucleoSpin column. The primer laczbw_s contains a 15 nucleotides overlap with the sequence of the pADL-10b phagemid vector (Antibody Design Labs, San Diego, Calif.) on the peptide leader pelB side of the first BglI site with a melting temperature of 58.4° C. (OligoAnalyzer 3.1, Integrated DNA Technologies, Inc., Coralville, Iowa) and the primer laczbw_r overlaps on the other side of the second BglI site with a melting temperature of 59° C. pADL-10b was cut by BglI and re-suspended at 20 ng/µl in pure water after purification over a Macherey Nagel NucleoSpin column.

The following reaction was prepared on ice in a PCR tube:

| Component | Amount | Volume |
| --- | --- | --- |
| Buffer 10x | | 3 µl |
| pADL10b BglI-cut (20 ng/µl) | 40 ng | 2 µl |
| Z900 DNA fragment (10 ng/µl) | 100 ng | 10 µl |
| T4 DNA polymerase (New England Biolabs, Ipswich, MA) | | 0.5 µl |
| Water | | 14.5 µl |
| Total Volume | | 30.0 µl |

The temperature was first raised to a plateau at 37° C. of variable length, followed by a one second plateau at 75° C., and a 10 minute plateau at 37° C. before the reaction was cooled down to 4° C. 50 µl of XL10-Gold bacteria (Agilent Technologies, San Diego, Calif.) made chemically-competent were transformed with 2 µl of the reaction mixture. After 30 min incubation on ice, the cells were heat-shocked for 30 seconds at 42° C., 150 µl of SOC medium were added and after 1 hour incubation at 37° C., 100 µl of each transformation were plated in duplicate on agar plates supplemented with ampicillin 100 µg/ml, IPTG and X-gal. Blue and white colonies were counted the day after.

The results of this experiment are depicted on FIG. 5. The shorter the incubation at 37° C., the higher is the number of blue colonies. Longer incubations resulted in lower cloning efficiency. This result clearly indicated that very short incubation times prior to heat inactivation of T4 DNA polymerase exonuclease activity gave the best conditions for an efficient rapid LIC method.

Example 4

Time Dependence of Annealing

The same reaction was performed from Example 3 with a 30 second plateau at 37° C. before the heat-mediated inactivation followed by an annealing plateau at 37° C. of variable length. The influence of RecA, a mediator of ssDNA annealing was also studied. Tth RecA, a thermostable form of RecA that survives the heat pulse at 75° C. was used (0.5 µl Tth RecA from New England Biolabs per reaction).

The experimental results are shown in FIG. 6. There was no apparent difference in cloning efficiency between no plateau at all and up to 10 min incubation at 37° C. These data clearly indicated that a short annealing plateau at 37° C. is sufficient to achieve significant cloning efficiency. As expected, in the presence of Tth RecA, the cloning efficiency was higher by about 70% in this experiment.

Example 5

Influence of RecA and ATP on Cloning Efficiency

The influence of Tth RecA was further studied with the same assay using a short temperature cycle consisting of a plateau of one second at 75° C. starting from a PCR machine pre-cooled and equilibrated at 4° C. and a one minute plateau at 37° C. before cooling the reaction back at 4° C. The overall cycle was completed between 2 and 3 min from the start of the temperature cycle to its return at 4° C. Also analyzed was the influence of ATP 1 mM which regulates the interaction of RecA with single-stranded DNA.

The experiment was done in tetraplicate (2 duplicates) and the data are shown as a graph on FIG. 7. A significant increase in the number of blue transformant was observed; 66% increase on average in the presence of RecA, further increased by another 47% in the presence of ATP. The overall increase in the presence of RecA and ATP was 145% higher than the control without RecA and ATP.

Example 6

Complementary Hemi-PCR Assay

In this example, a CH-PCR assay was performed by amplifying by PCR two halves of a phage DNA. The two fragments were joined in the conditions of Example 5 and the success of the reaction was quantified by a plaque assay after transformation in a bacterial host.

VCSM13 phage DNA was amplified with primer m13g5_s and m13g2_r (fragment V, 7270 bp) and phage CM13.9 was amplified with primers m13g2_s and m13g5_r (fragment C, 1448 bp). CM13.9 is a single mutant of M13KO7 containing the ir1A mutation (G→A mutation at position 8247).

Primer Sequence and Tm Estimation (OligoAnalyzer 3.1)

| Primer | Sequence | Length | Tm |
|---|---|---|---|
| m13g5_s | 5'-GAATATTTATGACGATTCCGCAGTATTG (SEQ ID NO: 3) | 28 | 54.4° C. |
| m13g5_r | 5'-CAATACTGCGGAATCGTCATAAATATTC (SEQ ID NO: 4) | 28 | 54.4° C. |
| m13g2_r | 5'-CGCGTTAAATTTTTGTTAAATCAGCTC (SEQ ID NO: 5) | 27 | 54.2° C. |
| m13g2_s | 5'-GAGCTGATTTAACAAAAATTTAACGCG (SEQ ID NO: 6) | 27 | 54.2° C. |

Polymerase Chain Reaction Conditions

| Component | Volume |
|---|---|
| Phusion 5x buffer | 10.0 µl |
| dNTP (2 mM) | 5.0 µl |
| DNA template 5 ng | 1.0 µl |
| Primer sense (10 µM) | 1.5 µl |
| Primer reverse (10 µM) | 1.5 µl |
| Hot Start Phusion polymerase (New England Biolabs, Ipswich, MA) | 0.5 µl |
| Water | 30.5 µl |
| Total Volume | 50.0 µl |

The final volume of the PCR reaction was 50 µl. After amplification for 25 cycles with annealing temperature at 57° C. and 3 min elongation, the template DNA was digested overnight at 37° C. after addition of DpnI restriction enzyme 1 µl directly in the PCR tube. Minigel analysis confirmed the amplification the two DNA fragments at the expected size. After purification over a Macherey Nagel NucleoSpin column and elution in water, the final DNA concentration was measured by UV spectrophotometry.

Rapid LIC Reaction:

| Component | Volume |
|---|---|
| Fragment V (60 ng) or water | 3.0 µl |
| Fragment C (60 ng) or water | 2.0 µl |
| Buffer 10x | 1.5 µl |
| T4 DNA polymerase (New England Biolabs, Ipswich, MA) | 0.5 µl |
| Water | 8.0 µl |
| Total Volume | 15 µl |

The final volume of the LIC reaction was 15 µl. After mixing all reagents on ice, the tubes were placed in PCR machine pre-cooled at 4° C. The temperature cycle was first a plateau at 37° C. of variable length, a plateau at 75° C. for 1 second, a plateau for 10 min at 37° C., then the temperature was brought back 4° C. XL10-Gold chemically competent bacterial cells 50 µl were transformed with 2 µl of the reaction by heat shock; 150 µl of SOB medium were added and the mixture was further incubated for 1 h at 37° C. 100 µl of the cells were mixed with 5 µl of TG1 Phage Competent™ cells (Antibody Design Labs, San Diego, Calif.) and 3 ml melted top agar at 50° C. and poured on a pre-warmed bottom agar plates. Plates were done in duplicate and plaques were counted the following morning.

The results are shown in FIG. 8. The cloning by LIC using our method resulted in a very large number of plaques only when the two complementary pieces of DNA were present in the reaction with very few plaques in both negative controls. There was no detectable influence of the length of the plateau in the timeframe that was tested; therefore, the shortest time is the preferred for the fastest reaction, similarly to the results in Example 3.

Example 7

Cloning of a Synthetic DNA Fragment in a Vector

In this example, a synthetic DNA fragment (scblue01, 885 bp) was cloned in the vector TGEX-FC (Antibody Design Labs, San Diego, Calif.). A 3482 bp-long fragment containing the bacterial origin of replication was amplified by PCR using TGEX-Fc plasmid DNA as a template and the primers bsarem_s and tgex_S3rev. The areas of homology in the scblue01 fragment are underlined in the hereafter table; the homologies are both 22-bp long with a Tm of 60.4° C. and 64.4° C. respectively (OligoAnalyzer 3.1, Integrated DNA Technologies, Inc.). Examination by minigel analysis of the PCR reaction showed a unique band at the expected size; the PCR reaction was purified over a Macherey Nagel NucleoSpin column and eluted in water at the concentration of 20 ng/µl.

Primers and DNA Fragment

| Primer | Sequence | Length |
|---|---|---|
| bsarem_s | 5'-TCCAACAAAGCCCTCCCAGC (SEQ ID NO: 7) | 20 |
| tgex_S3rev | 5'-GACTGTGACTGGTTAGACGCCT (SEQ ID NO: 8) | 22 |

Synthetic DNA

| | | |
|---|---|---|
| scblue01 | 5'-<u>AGGCGTCTAACCAGTCACAGTCGCA</u>AGTTTAAACGGATCTCTAGCGAATTCGGCTTGGGGATATCCACCATGGAG | 885 bp |

| Primer | Sequence | Length |
|---|---|---|
| | ACAGACACACTCCTGCTATGGGTAC | |
| | TGCTGCTCTTAGCGGCCCAGCCGGC | |
| | CATGGCGCCAATACGCAAACCGCC | |
| | TCTCCCCGCGCGTTGGCCGATTCAT | |
| | TAATGCAGCTGGCACGACAGGTTTC | |
| | CCGACTGGAAAGCGGGCAGTGAGCG | |
| | CAACGCAATTAATGTGAGTTAGCTC | |
| | ACTCATTAGGCACCCCAGGCTTTAC | |
| | ACTTTATGCTTCCGGCTCGTATGTT | |
| | GTGTGGAATTGTGAGCGGATAACAA | |
| | TTTCACACAGGAAACAGCTATGACC | |
| | ATGATTACGGATTCACTGGCCGTCG | |
| | TTTTACAACGTCGTGACTGGGAAAA | |
| | CCCTGGCGTTACCCAACTTAATCGC | |
| | CTTGCAGCACATCCCCCTTTCGCCA | |
| | GCTGGCGTAATAGCGAAGAGGCCCG | |
| | CACCGATCGCCCTTCCCAACAGTTG | |
| | CGCAGCCTGAATTAAAATAGATAGG | |
| | GCCCGGGAGGCCCCGAGCCCAAATC | |
| | TTCTGACAAAACTCACACATGCCCA | |
| | CCGTGCCCAGCACCTGAACTCCTGG | |
| | GGGGACCGTCAGTCTTCCTCTTCCC | |
| | CCCAAAACCCAAGGACACCCTCATG | |
| | ATCTCCCGGACCCCTGAGGTCACAT | |
| | GCGTGGTGGTGGACGTGAGCCACGA | |
| | AGACCCTGAGGTCAAGTTCAACTGG | |
| | TACGTGGACGGCGTGGAGGTGCATA | |
| | ATGCCAAGACAAAGCCGCGGGAGGA | |
| | GCAGTACAACAGCACGTACCGTGTG | |
| | GTCAGCGTCCTCACCGTCCTGCACC | |
| | AGGACTGGCTGAATGGCAAGGAGTA | |
| | CAAGTGCAAGGTGTCCAACAAAGCC | |
| | CTCCCAGCCC (SEQ ID NO: 9) | |

Rapid LIC Reaction

| Component | Volume |
|---|---|
| T4 DNA polymerase 10x buffer | 2.0 µl |
| ATP 10 mM | 2.0 µl |
| T4 DNA polymerase (New England Biolabs) | 0.25 µl |
| Th Rec A (New England Biolabs) | 0.25 µl |
| scblue01 20 ng/µl | 0.6 µl |
| PCR product 20 ng/µl | 2.5 µl |
| water | 12.4 µl |
| Total | 20 µl |

All components were mixed on ice in a single PCR tube and the tube transferred to a PCR machine pre-cooled at 4° C. A temperature cycle made of a 1 second plateau at 75° C. followed by a 1 min plateau at 37° C. before cooling back at 4° C. was then initiated; the cycle was completed in 3 min. Chemically competent XL10-gold bacteria were transformed and plated on an agar plate supplemented with ampicillin. The day after, three colonies were picked and grown overnight at 37° C. with shaking. Sequence analysis revealed the presence of the synthetic DNA sequence properly inserted in all 3 colonies.

Example 8

Cloning of a PCR Fragment in a Vector

In this example, the HyHEL-10 scFv was cloned into the TGEX-SCblue vector build in Example 7. The HyHEL-10 scFv fragment was amplified from a phagemid clone derived from the pADL-10b vector (Antibody Design Labs, San Diego, Calif.) with the HyHEL-10 scFv sequence inserted in the double SfiI cloning site using the primers scFvblue_s and scFvblue_r. A single band at the expected size was found by minigel analysis. After treatment by DpnI to cut the methylated template DNA, the PCR product was purified over a Macherey Nagel NucleoSpin column and eluted in water at the concentration of 10 ng/µl. TGEX-SCblue vector was cut by SfiI; the reaction mixture was purified over a Macherey Nagel NucleoSpin column and eluted in water at the concentration of 75 ng/µl.

Primers and PCR fragment; Tm estimation (OligoAnalyzer 3.1) are given for the sequence overlaps with the cut vector (underlined).

| Primer | Sequence | Homologies Length | Tm |
|---|---|---|---|
| scFvblue_s | 5'-__tgctgctcttagcggcccagccggccatggcg__ GATATTGTGCTAACTCAGTC (SEQ ID NO: 10) | 18 | 60.8° C. |
| scFvblue_r | 5'-__aagatttgggctcggggcct__cccgggcc TGCAGAGACAGTGACCAGAG (SEQ ID NO: 11) | 20 | 61.9° C. |

-continued

| Primer | Sequence | Homologies Length | Tm |
|---|---|---|---|
| DNA Fragment | | | |
| HyHEL-10 scFv | 5'-GATATTGTGCTAACTCAGTCTCCAG<br>CCACCCTGTCTGTGACTCCAGGAAATAG<br>CGTCAGTCTTTCCTGCAGGGCCAGCCAA<br>AGTATTGGCAACAACCTACACTGGTATC<br>AACAAAAATCACATGAGTCTCCAAGGCT<br>TCTCATCAAGTATGCTTCCCAGTCCATC<br>TCTGGGATCCCCTCCAGGTTCAGTGGCA<br>GTGGATCAGGGACAGATTTCACTCTCAG<br>TATCAACAGTGTGGAGACTGAAGATTTT<br>GGAATGTATTTCTGTCAACAGAGTAACA<br>GCTGGCCTTACACGTTCGGAGGGGGGAC<br>CAAGCTGGAAATAAAAGGTGGTGGTGGT<br>TCTGGTGGTGGTGGTTCTGGCGGCGGCG<br>GCTCCGGTGGTGGTGGATCCGACGTGCA<br>GCTTCAGGAGTCAGGACCTAGCCTCGTG<br>AAACCTTCTCAGACTCTGTCCCTCACCT<br>GTTCTGTCACTGGCGACTCCATCACCAG<br>TGATTACTGGAGCTGGATCCGGAAATTC<br>CCAGGGAATAGACTTGAGTACATGGGGT<br>ACGTAAGCTACAGTGGTAGCACTTACTA<br>CAATCCATCTCTCAAAAGTCGAATCTCC<br>ATCACCCGAGACACATCCAAGAACCAGT<br>ACTACCTGGATTTGAATTCTGTGACTAC<br>TGAGGACACAGCCACATATTACTGTGC<br>AAACTGGGACGGTGATTACTGGGGCCA<br>AGGGACTCTGGTCACTGTCTCTGCA<br>(SEQ ID NO: 12) | | |

Rapid LIC Reaction

| Component | Volume |
|---|---|
| T4 DNA polymerase 10x buffer | 2.0 µl |
| ATP 10 mM | 2.0 µl |
| T4 DNA polymerase (New England Biolabs) | 0.25 µl |
| Th Rec A (New England Biolabs) | 0.25 µl |
| HyHEL-10 scFv 10 ng/µl | 3.5 µl |
| TGEX-SCblue SfiI cut 75 ng/µl | 1 µl |
| Water | 11 µl |
| Total | 20 µl |

The rapid LIC method was identical to the procedure in Example 7. Fifty microliter (50 µl) of chemically competent XL10-gold cells were transformed by heat shock with 2 µl of the reaction, resuspended in 200 µl SOC medium and, after 1 hour incubation at 37° C. with shaking, plated on agar plates supplemented with ampicillin, IPTG and X-gal. The day after, around half of the colonies were white. Four white colonies were picked, grown overnight in 3-ml 2×YT medium supplemented with ampicillin, and sequence analysis of two colonies showed proper insertion of the scFv PCR fragment.

Example 9

Insertion of Two Complementary Oligonucleotides in a Vector

In this example a large loop in a DNA sequence was inserted. This type of cloning project is known to be difficult because of the presence of secondary structures. The recipient vector contained a lambda t1 terminator (lt1) where the terminator loop had been replaced by an XbaI site (underlined):

(SEQ ID NO: 13)
5'-CAGTCACTATGAATCAACTACTTAGATGGTATTAGTGACCTGTA<u>TCT AGA</u>ATTTTTTGTCATCAAACCTGTCGCACTCC

Two oligonucleotides containing homology areas with the truncated lt1 sequence on each side of the XbaI site and complementary on their 3' ends were designed to complete the entire lt1 terminator sequence after insertion in the XbaI site. Below, the sequence homologies with the vector are underlined while the complementary sequence between the two oligonucleotides have been boxed (length 18, Tm 45.1° C.).

Primers

| Primer | Sequence | Homology Length | Tm |
|---|---|---|---|
| lt1loopA_s | 5'-<u>TGGTATTAGTGACCTGTA</u><br>ACAGAGCATTAGCG CAAGGTGATTTTTGTCTT<br>(SEQ ID NO: 14) | 18 | 46.2° C. |

-continued

| Primer | Sequence | Homology Length | Tm |
|---|---|---|---|
| lt1loopB_r | 5'-GTTTGATGACAAAAAAT TAGCGCAAG|AAGACAAAAATCACCTTG| (SEQ ID NO: 15) | 17 | 39.7° C. |

Three hundred nanogram (300 ng) of the recipient vector 23C1HH10S.2 were digested in a 10 µl reaction volume with XbaI for 3 hours. The cut vector was purified over a Macherey Nagel NucleoSpin column and eluted in 15 µl of water.

Rapid LIC Reaction

| Component | Volume |
|---|---|
| T4 DNA polymerase 10x buffer | 2.0 µl |
| ATP 10 mM | 2.0 µl |
| T4 DNA polymerase (New England Biolabs) | 0.5 µl |
| Th Rec A (New England Biolabs) | 0.5 µl |
| 23C1HH10S.2 cut | 12 µl |
| Water | 2 µl |
| Total | 19 µl |

The rapid LIC method was identical to the procedure in Example 7. After completion of the temperature cycle, 1 µl of an equimolar mixture of the two oligonucleotides at 1 µM each in water was added to the reaction and the temperature cycle used in Example 7 was run a second time. Clone analysis after bacterial transformation revealed a high proportion of parental clones; colony PCR followed by restriction analysis with XbaI of 16 colonies found 2 colonies missing the XbaI site. Sequence analysis of these two clones found the proper insertion of the two oligonucleotides, thus creating a complete lt1 terminator.

Example 10

Insertion of Two DNA Fragments in a Vector

In this example, the variable human heavy chain domain of a human antibody was cloned together with a modified CH1 domain of human IgG1 into the backbone of the TGEX-HC vector (Antibody Design Labs, San Diego, Calif.). The resulting plasmid in association with a light chain expressing vector can be used to express a recombinant Fab fragment.

Primers and DNA Fragments

| Primer | Sequence | Homology Length | Tm |
|---|---|---|---|
| tgexhug1ch1_s | 5'-|GCATCCACCAAGGGCCCATC| (SEQ ID NO: 16) | 20 | 61.6° C. |
| tgexhug1hgtht_r | 5'-|AGGTCGGGGGATCTGC|GGCCGCTCA TGTGTGAGTTTTGTCACAAGATTTGG GCTCAACTTTCTTGTCC (SEQ ID NO: 17) | 16 | 56.6° C. |

| DNA Fragments | Characteristics | Length |
|---|---|---|
| Vector | TGEX-HC, BssHII-NotI cut, gel purified | 3292 bp |
| V Domain | Synthetic DNA fragment | 395 bp |
| CH1 domain | DNA fragment prepared by PCR amplification using the above primers and TGEX-HC as template | 349 bp |

| Homologies | | Length | Tm |
|---|---|---|---|
| Vector/V Domain | 5' TTCTGTGTTCTCTCCACAGG (SEQ ID NO: 18) | 20 | 53.1° C |
| V Domain/CH1 | 5'-GCATCCACCAAGGGCCCATC (SEQ ID NO: 19) | 20 | 61.6° C. |

| Homologies | | Length | Tm |
|---|---|---|---|
| CH1/Vector | 5'-GCAGATCCCCCGACCT (SEQ ID NO: 20) | 16 | 56.6° C. |

Rapid LIC Reaction

| Component | Volume/Quantity |
|---|---|
| T4 DNA polymerase 10x buffer | 2.0 µl |
| ATP 10 mM | 2.0 µl |
| T4 DNA polymerase (New England Biolabs) | 0.5 µl |
| Th Rec A (New England Biolabs) | 0.5 µl |
| vector | 50 ng |
| V Domain | 18.8 ng |
| CH1 Domain | 24 ng |
| Water | 2 µl |
| Total | 20 µl |

The rapid LIC method was identical to the procedure in Example 7. Fifty microliter (50 µl) of chemically competent XL10-gold cells were transformed by heat shock with 2 µl of the reaction, resuspended in 200 µl SOC medium and, after 1 hour incubation at 37° C. with shaking, plated on agar plates supplemented with ampicillin, IPTG and X-gal. The day after, around half of the colonies were white. Four colonies were picked, grew overnight in 3-ml 2×YT medium supplemented with ampicillin, and sequence analysis of two colonies showed proper assembly of the 2 fragments in the DNA vector.

Example 11

Manual Rapid LIC Reaction with a Heated Water Bath

In this example, the cloning efficiency was analyzed by incubating the rapid LIC reaction in a heated water bath for varied periods of time.

Rapid LIC Reaction

| Component | Amount | Volume |
|---|---|---|
| Buffer 10x | | 2 µl |
| ATP 10 mM | | 2 µl |
| pADL10b BglI-cut (25 ng/µl) | 50 ng | 2 µl |
| Z900 DNA fragment (25 ng/µl) | 50 ng | 2 µl |
| T4 DNA polymerase (New England Biolabs) | | 0.5 µl |
| Th Rec A (New England Biolabs) | | 0.5 µl |
| Water | | 11 µl |
| Total Volume | | 20.0 µl |

All components were mixed on ice in a single PCR tube and immersed for a short period of time in a water bath preheated at 75° C. before being brought back on ice. Each assay was done in duplicate as well as a control with the help of a PCR machine as described in Example 7. Chemically competent XL10-gold bacteria were transformed and plated on agar plates supplemented with ampicillin, IPTG and X-gal and incubated overnight at 37° C. The morning after, blue and white colonies were counted.

Results. Average blue and white colony counts are given for incubation in a 75° C. water bath for 2 s, 5 s, 10 s and for a rapid LIC reaction made using a PCR machine. The percentage of blue colonies, resulting from the proper insertion of the alpha fragment of the beta-galactosidase in the vector, were close to 80% on average, below the percentage observed for a reaction done with a PCR machine (95%), but still in the range of a very satisfying cloning efficiency.

| Time (s) | Blue Colonies | White Colonies | Percentage Blue |
|---|---|---|---|
| 2 | 58 | 17.5 | 77% |
| 5 | 32.5 | 9 | 78% |
| 10 | 34 | 9 | 79% |
| PCR | 55 | 3 | 95% |

TABLE 1

| Sequence Unfolding at 75° C. | | | | | | |
|---|---|---|---|---|---|---|
| Source | Sequence Unfolded[3] | | Length | $\Delta H^1$ Kcal/mol | ° C. (salt) | $Tm^2$ % |
| | polyA(15) | | 15 | 112 | 28.4 | 100.0 |
| | polyA(20) | | 20 | 152 | 37.3 | 100.0 |
| | polyG(15) | | 15 | 152.6 | 69.3 | 89.9 |
| | polyG(20) | | 20 | 207.1 | 78.7 | 36.7 |
| Example 3 | tactcgcggcccagc ccaccgccttggcct (SEQ ID NO: 21) | | 15 15 | 134 134.3 | 58.4 59 | 99.4 99.3 |
| Example 6 | gaatatttatgacgattccgcagtattg gagctgatttaacaaaaatttaacgcg (SEQ ID NO: 22) | | 28 27 | 218 215 | 54.4 54.2 | 100.0 100.0 |

TABLE 1-continued

Sequence Unfolding at 75° C.

| Source | Sequence Unfolded[3] | Length | ΔH[1] Kcal/mol | ° C. (salt) | Tm[2] % |
|---|---|---|---|---|---|
| Example 7 | aggcgtctaaccagtcacagtc tccaacaaagccctcccagccc (SEQ ID NO: 23) | 22 22 | 183.1 192.7 | 58.7 64.4 | 99.9 99.1 |
| Example 8 | tgctgctcttagcggccc aagatttgggctcggggcct (SEQ ID NO: 24) | 18 20 | 152.7 173.4 | 60.8 61.9 | 99.4 99.5 |
| Example 9 | tggtattagtgacctgta ctttgatgacaaaaaat (SEQ ID NO: 25) | 18 17 | 139.4 128.2 | 46.2 39.7 | 100.0 100.0 |

[1]Enthalpy values were estimated using OligoCal (Kibbe 2007).
[2]Tm values were estimated using OligoAnalyzer 3.1 (www.idtdna.com/calc/analyzer).
[3]Unfolded fractions were calculated according to Batcher et al. (2005).

The foregoing disclosure of the preferred embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequence may be varied and still remain within the spirit and scope of the present subject disclosure.

REFERENCES

1. Aslanidis C, de Jong P J. Ligation-independent cloning of PCR products (LIC-PCR). Nucleic Acids Res. 1990; 18(20):6069-74.
2. Aslanidis C, de Jong P J, Schmitz G. Minimal length requirement of the single-stranded tails for ligation-independent cloning (LIC) of PCR products. PCR Methods Appl. 1994; 4(3):172-7.
3. Bitinaite J, Rubino M, Varma K H, Schildkraut I, Vaisvila R, Vaiskunaite R. USER friendly DNA engineering and cloning method by uracil excision. Nucleic Acids Res. 2007; 35(6):1992-2002.
4. Büttcher A, Kowerko D, Sigel R K. Explicit analytic equations for multimolecular thermal melting curves. Biophys Chem. 2015; 202:32-9.
5. Breslauer K J, Frank R, Blocker H, Marky L A. Predicting DNA duplex stability from the base sequence. Proc Natl Acad Sci USA. 1986 June; 83(11):3746-50.
6. Cohen, S. N., A. C. Chang, H. W. Boyer and R. B. Helling. Construction of biologically functional bacterial plasmids in vitro. Proc. Nat. Acad. Sci. USA 1973; 70:3204-3244.
7. Donahue W F, Turczyk B M, Jarrell K A. Rapid gene cloning using terminator primers and modular vectors. Nucleic Acids Res. 2002; 30(18):e95.
8. Gal J, Schnell R, Szekeres S, Kalman M. Directional cloning of native PCR products with preformed sticky ends (autosticky PCR). Mol Gen Genet. 1999; 60(6):569-73.
9. Gibson, D. G. Enzymatic assembly of overlapping DNA fragments. Methods in Enzymology 2011; 498, 349-61.
10. Hamilton M D, Nuara A A, Gammon D B, Buller R M, Evans D H. Duplex strand joining reactions catalyzed by vaccinia virus DNA polymerase. Nucleic Acids Res. 2007; 35(1):143-51.
11. Haun, R. S., I. M. Serventi, et al. "Rapid, reliable ligation-independent cloning of PCR products using modified plasmid vectors." Biotechniques 1992; 13(4): 515-8.
12. Horton R M, Hunt H D, Ho S N, Pullen J K, Pease L R. Engineering hybrid genes without the use of restriction enzymes: gene splicing by overlap extension. Gene. 1989; 77(1):61-8.
13. Hsiao K. Exonuclease III induced ligase-free directional subcloning of PCR products. Nucleic Acids Res. 1993; 21(23):5528-9.
14. Jones D H, Howard B H. A rapid method for site-specific mutagenesis and directional subcloning by using the polymerase chain reaction to generate recombinant circles. Biotechniques. 1990; 8(2):178-183.
15. Jones D H, Sakamoto K, Vorce R L, Howard B H. DNA mutagenesis and recombination. Nature. 1990; 344 (6268):793-794.
16. Kaluz S, Kolble K, Reid K B. Directional cloning of PCR products using exonuclease III. Nucleic Acids Res. 1992; 20(16):4369-70.
17. Kibbe W A. OligoCalc: an online oligonucleotide properties calculator. Nucleic Acids Res. 2007; 35:W43-6.
18. Kowalczykowski S C. Biochemistry of genetic recombination: energetics and mechanism of DNA strand exchange. Annu Rev Biophys Biophys Chem. 1991; 20:539-75.
19. Kuijper J L, Wiren K M, Mathies L D, Gray C L, Hagen F S. Functional cloning vectors for use in directional cDNA cloning using cohesive ends produced with T4 DNA polymerase. Gene 1992; 112(2):147-55.
20. Mergny J L, Lacroix L. Analysis of thermal melting curves. Oligonucleotides. 2003; 13(6):515-37.
21. SantaLucia J Jr. A unified view of polymer, dumbbell, and oligonucleotide DNA nearest-neighbor thermodynamics. Proc Natl Acad Sci USA, 1998; 95(4):1460-1465.
22. Stoker A W. Cloning of PCR products after defined cohesive termini are created with T4 DNA polymerase. Nucleic Acids Res. 1990; 18(14):4290.
23. Li C, Evans R M. Ligation independent cloning irrespective of restriction site compatibility. Nucleic Acids Res. 1997; 25(20):4165-6.
24. Li M Z, Elledge S J. Harnessing homologous recombination in vitro to generate recombinant DNA via SLIC. Nat Methods. 2007; 4(3):251-6.
25. Tachibana A, Tohiguchi K, Ueno T, Setogawa Y, Harada A, Tanabe T. Preparation of long sticky ends for universal ligation-independent cloning: sequential T4 DNA polymerase treatments. J Biosci Bioeng. 2009; 107(6):668-9.
26. Thieme F, Engler C, Kandzia R, Marillonnet S. Quick and clean cloning: a ligation-independent cloning strategy for selective cloning of specific PCR products from non-specific mixes. PLoS One. 2011; 6(6):e20556
27. Tillett D, Neilan B A. Enzyme-free cloning: a rapid method to clone PCR products independent of vector restriction enzyme sites. Nucleic Acids Res. 1999; 27(19): e26.
28. Tseng H. DNA cloning without restriction enzyme and ligase. Biotechniques. 1999; 27(6):1240-4.
29. Willer D O, Yao X D, Mann M J, Evans D H. In vitro concatemer formation catalyzed by vaccinia virus DNA polymerase. Virology. 2000 20; 278(2):562-9.
30. Yang Y S, Watson W J, Tucker P W, Capra J D. Construction of recombinant DNA by exonuclease recession. Nucleic Acids Res. 1993; 21(8):1889-93.
31. Yang J, Zhang Z, Zhang X A, Luo Q. A ligation-independent cloning method using nicking DNA endonuclease. Biotechniques. 2010; 49(5):817-21.

All the references cited herein, including patents, patent applications, and publications, and including references cited in the Bibliography, are incorporated by reference in their entireties.

Headings are for the convenience of the reader and do not limit the scope of the invention.

What is claimed is:

1. A method of cloning DNA using T4 DNA polymerase comprising:
   a) combining linear DNA fragments having terminal sequence homologies between 15 and 100 nucleotides;
   b) generating single-stranded recesses by adding the T4 DNA polymerase to the linear DNA fragments; and
   c) treating the T4 DNA polymerase with heat at a temperature between 50° C. and 95° C. for a time of 10 seconds.

2. The method according to claim 1, wherein steps a) through c) are completed in 1 minute.

3. The method according to claim 1, wherein steps a) through c) are completed in less than 3 minutes.

4. The method according to claim 1, wherein steps a) through c) are completed in less than 5 minutes.

5. A method of cloning DNA using T4 DNA polymerase comprising:
   a) combining linear DNA fragments having terminal sequence homologies between 15 and 100 nucleotides;
   b) generating single-stranded recesses by adding the T4 DNA polymerase to the linear DNA fragments; and
   c) treating the T4 DNA polymerase with heat at a temperature of 75° C. for 5 seconds.

6. A method of cloning DNA using T4 DNA polymerase comprising:
   a) combining linear DNA fragments having terminal sequence homologies between 15 and 100 nucleotides;
   b) generating single-stranded recesses by adding the T4 DNA polymerase to the linear DNA fragments; and
   c) treating the T4 DNA polymerase with heat at a temperature of 50° C. for a time of 1 minute.

* * * * *